(12) United States Patent
Chettibi et al.

(10) Patent No.: US 8,304,388 B2
(45) Date of Patent: Nov. 6, 2012

(54) IMAGING AGENTS

(75) Inventors: Salah Chettibi, Amersham (GB); Ben Newton, Amersham (GB); Mette Husbyn, Oslo (NO); Magne Solbakken, Skien (NO); Peter Brian Iveson, Amersham (GB); Rajiv Bhalla, Amersham (GB); Daniel Kramer, Mount Sinai, NY (US); Jane Brown, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 881 days.

(21) Appl. No.: 12/302,290

(22) PCT Filed: May 25, 2007

(86) PCT No.: PCT/GB2007/001964
§ 371 (c)(1),
(2), (4) Date: Nov. 25, 2008

(87) PCT Pub. No.: WO2007/138291
PCT Pub. Date: Dec. 6, 2007

(65) Prior Publication Data
US 2009/0191123 A1    Jul. 30, 2009

(30) Foreign Application Priority Data

May 25, 2006  (GB) .................... 0610395.6

(51) Int. Cl.
*A61K 38/39* (2006.01)
*A61K 38/10* (2006.01)
*A61K 38/08* (2006.01)

(52) U.S. Cl. ............... 514/17.2; 514/21.4; 514/21.6; 424/1.69; 424/9.341

(58) Field of Classification Search ........... None
See application file for complete search history.

(56) References Cited

U.S. PATENT DOCUMENTS

| 5,741,670 | A  | 4/1998 | Goetinck et al. |
| 5,972,890 | A  | 10/1999 | Lees et al. |
| 2005/0048063 | A1 | 3/2005 | Ruoslahti et al. |

FOREIGN PATENT DOCUMENTS

| WO |   9321226 | 10/1993 |
| WO | 2005/049005 | 6/2005 |
| WO | 2005/053752 | 6/2005 |
| WO | 2005/082941 | 9/2005 |
| WO | 2006/020743 | 2/2006 |
| WO | 2006/032911 | 3/2006 |
| WO | WO 2006/054904 | * 5/2006 |

OTHER PUBLICATIONS

GB0610395.6 Search Report dated Sep. 2006.
PCT/GB2007/001964 Int'l Search Report Written Opinion dated Apr. 2008.
Chiang, et.al. "A synthetic peptide derived from the sequence of a type I collagen receptor inhibits type I collagen-mediated platelet aggregation" Journal of Clinical Investigation, NY, NY vol. 100, No. 8, Oct. 1997, pp. 2079-2084.
Chiang, Thomas "A synthetic nonapeptide derived from the sequence of a platelet type I collagen receptor inhibits type I collagen-mediated platelet aggregation" American Journal of Medical Sciences, XX, XX, vol. 320 No. 6 Dec. 200, pp. 362-367.
Chiang, T, et.al. "Cloning, characterization, and functional studies of a 47-kDa platelet receptor for type III collagen" Journal of Biological Chemistry, vol. 277, No. 38, Sep. 2002, pp. 24896-34901.
Krahn, et.al. "Fluorescently labeled collagent binding proteins allow specific visualization of collagen in tissues and live cell culture" Analytical Biochemistry, Academic Press, NY, NY, vol. 350, No. 2 Mar. 2006, pp. 177-185.

* cited by examiner

*Primary Examiner* — Christina Bradley

(57) ABSTRACT

The present invention provides a novel imaging agent suitable for the non-invasive visualization of fibrosis. A precursor for the preparation of the imaging agent is also provided by the invention, as well as a pharmaceutical composition comprising the imaging agent and a kit for the preparation of the pharmaceutical composition. In a further aspect, use of the imaging agent for in vivo imaging and in the preparation of a medicament for the diagnosis of a condition which comprises fibrosis is provided.

7 Claims, 1 Drawing Sheet

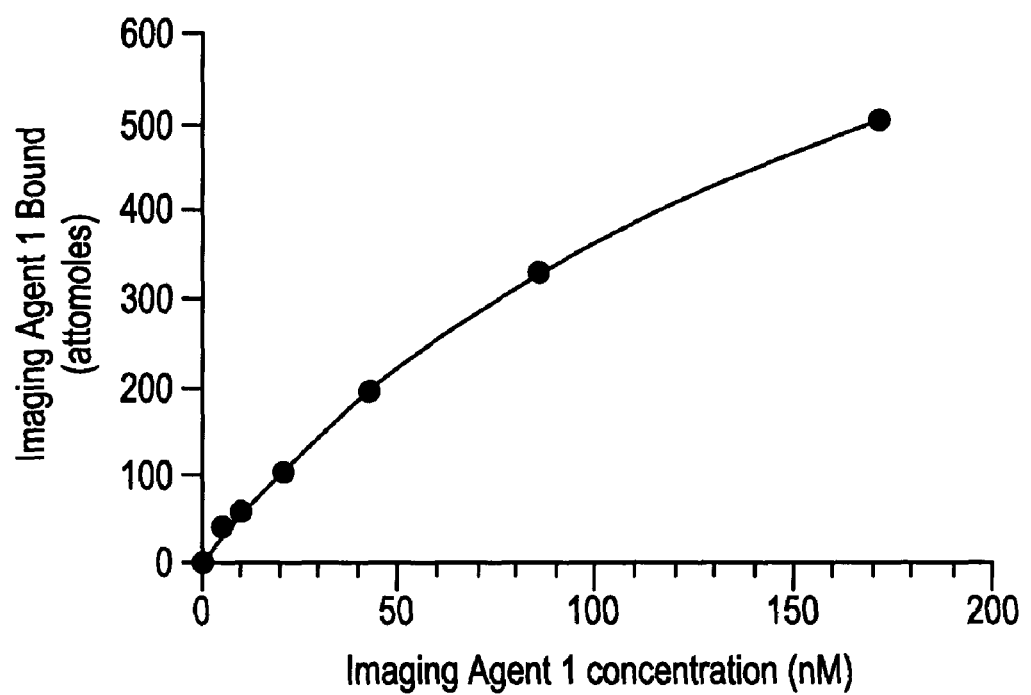

SEQUENCE LISTING

<160> NUMBER OF SEQ ID NOS: 35

<210> SEQ ID NO 1
<211> LENGTH: 16
<212> TYPE: PRT
<213> ORGANISM: Artificial
<220> FEATURE:
<223> OTHER INFORMATION: Peptide synthesised on an automated
      synthesiser.
<220> FEATURE:
<221> NAME/KEY: X
<222> LOCATION: (13)..(13)
<223> OTHER INFORMATION: Residue X can be any of cysteine,
      2-aminobutyric acid, methionine or alanine.

<400> SEQUENCE: 1

Ala Asn Ala Ala Leu Lys Ala Gly Glu Leu Tyr Lys Xaa Ile Leu Tyr
1               5                   10                  15

<210> SEQ ID NO 2
<211> LENGTH: 18
<212> TYPE: PRT
<213> ORGANISM: Artificial
<220> FEATURE:
<223> OTHER INFORMATION: Peptide synthesised on an automated
      synthesiser.
<220> FEATURE:
<221> NAME/KEY: X
<222> LOCATION: (15)..(15)
<223> OTHER INFORMATION: Residue X can be any of cysteine,
      2-aminobutyric acid, methionine or alanine.

<400> SEQUENCE: 2

Arg Arg Ala Asn Ala Ala Leu Lys Ala Gly Glu Leu Lys Lys Xaa Ile
1               5                   10                  15

Leu Lys

<210> SEQ ID NO 3
<211> LENGTH: 16
<212> TYPE: PRT
<213> ORGANISM: Artificial
<220> FEATURE:
<223> OTHER INFORMATION: Peptide synthesised on an automated
      synthesiser.
<220> FEATURE:
<221> NAME/KEY: X
<222> LOCATION: (4)..(4)
<223> OTHER INFORMATION: Residue X can be any of cysteine,
      2-aminobutyric acid, methionine or alanine.

<400> SEQUENCE: 3

Tyr Leu Ile Xaa Lys Tyr Leu Glu Gly Ala Lys Leu Ala Ala Asn Ala
1               5                   10                  15

<210> SEQ ID NO 4
<211> LENGTH: 18
<212> TYPE: PRT
<213> ORGANISM: Artificial
<220> FEATURE:
<223> OTHER INFORMATION: Peptide synthesised on an automated
      synthesiser.
<220> FEATURE:
<221> NAME/KEY: X
<222> LOCATION: (4)..(4)
<223> OTHER INFORMATION: Residue X can be any of cysteine,
      2-aminobutyric acid, methionine or alanine
<220> FEATURE:
<221> NAME/KEY: X
<222> LOCATION: (4)..(4)
<223> OTHER INFORMATION: Residue X can be any of cysteine, 2-aminobutyric acid, methionine or alanine.

<400> SEQUENCE: 4

Lys Leu Ile Xaa Lys Lys Leu Glu Gly Ala Lys Leu Ala Ala Asn Ala
1               5                   10                  15

Arg Arg

<210> SEQ ID NO 5
<211> LENGTH: 9
<212> TYPE: PRT
<213> ORGANISM: Artificial
<220> FEATURE:
<223> OTHER INFORMATION: Peptide synthesised on an automated
      synthesiser.

<400> SEQUENCE: 5

Gly Glu Leu Tyr Lys Cys Ile Leu Tyr
1               5

<210> SEQ ID NO 6
<211> LENGTH: 11
<212> TYPE: PRT
<213> ORGANISM: Artificial
<220> FEATURE:
<223> OTHER INFORMATION: Peptide synthesised on an automated
      synthesiser.

<400> SEQUENCE: 6

Cys Asp Ala Arg Lys Ser Glu Val Gln Lys Cys
1               5                   10

<210> SEQ ID NO 7
<211> LENGTH: 8
<212> TYPE: PRT
<213> ORGANISM: Artificial
<220> FEATURE:
<223> OTHER INFORMATION: Peptide synthesised on an automated
      synthesiser.

<400> SEQUENCE: 7

Lys Glu Leu Asn Leu Val Tyr Thr
1               5

<210> SEQ ID NO 8
<211> LENGTH: 10
<212> TYPE: PRT
<213> ORGANISM: Artificial
<220> FEATURE:
<223> OTHER INFORMATION: Peptide synthesised on an automated
      synthesiser.

<400> SEQUENCE: 8

Cys Lys Glu Leu Asn Val Leu Tyr Thr Cys
1               5                   10

<210> SEQ ID NO 9
<211> LENGTH: 10
<212> TYPE: PRT
<213> ORGANISM: Artificial
<220> FEATURE:
<223> OTHER INFORMATION: Peptide synthesised on an automated
      synthesiser.

<400> SEQUENCE: 9

Cys Lys Glu Leu Asn Leu Val Tyr Thr Cys
1               5                   10

```
<210> SEQ ID NO 10
<211> LENGTH: 8
<212> TYPE: PRT
<213> ORGANISM: Artificial
<220> FEATURE:
<223> OTHER INFORMATION: Peptide synthesised on an automated
      synthesiser.

<400> SEQUENCE: 10

Cys Val Trp Leu Trp Glu Gln Cys
1               5

<210> SEQ ID NO 11
<211> LENGTH: 8
<212> TYPE: PRT
<213> ORGANISM: Artificial
<220> FEATURE:
<223> OTHER INFORMATION: Peptide synthesised on an automated
      synthesiser.

<400> SEQUENCE: 11

Cys Val Trp Leu Trp Glu Asn Cys
1               5

<210> SEQ ID NO 12
<211> LENGTH: 9
<212> TYPE: PRT
<213> ORGANISM: Artificial
<220> FEATURE:
<223> OTHER INFORMATION: Peptide synthesised on an automated
      synthesiser.

<400> SEQUENCE: 12

Cys Val Trp Thr Leu Pro Asp Gln Cys
1               5

<210> SEQ ID NO 13
<211> LENGTH: 16
<212> TYPE: PRT
<213> ORGANISM: Artificial
<220> FEATURE:
<223> OTHER INFORMATION: Peptide synthesised on an automated
      synthesiser.
<220> FEATURE:
<221> NAME/KEY: X
<222> LOCATION: (13)..(13)
<223> OTHER INFORMATION: X can be any of cysteine, 2-aminobutyric
      acid, methionine or alanine.

<400> SEQUENCE: 13

Ala Asn Ala Ala Leu Lys Ala Gly Glu Leu Tyr Lys Xaa Ile Leu Phe
1               5                   10                  15

<210> SEQ ID NO 14
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (15)..(15)
<223> OTHER INFORMATION: Xaa can be any naturally occurring amino acid

<400> SEQUENCE: 14

Arg Arg Ala Asn Ala Ala Leu Lys Ala Gly Glu Leu Tyr Lys Xaa Ile
1               5                   10                  15

Leu Tyr
```

```
<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 15

Gly Glu Leu Tyr Lys Xaa Ile Leu Tyr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 16

Asp Ala Arg Lys Ser Glu Val Gln Lys
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 17

Lys Glu Leu Asn Val Leu Tyr Thr
1               5

<210> SEQ ID NO 18
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 18

Ala Asn Ala Ala Leu Lys Ala Gly Glu Leu Tyr Lys Cys Ile Leu Tyr
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (13)..(13)
<223> OTHER INFORMATION: Xaa is Abu

<400> SEQUENCE: 19

Ala Asn Ala Ala Leu Lys Ala Gly Glu Leu Tyr Lys Xaa Ile Leu Tyr
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: misc_feature
<222> LOCATION: (13)..(13)
<223> OTHER INFORMATION: Xaa = Abu

<400> SEQUENCE: 20

Ala Asn Ala Ala Leu Lys Ala Gly Glu Leu Tyr Lys Xaa Ile Leu Phe
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (12)..(12)
<223> OTHER INFORMATION: Xaa = NMeLys
<220> FEATURE:
<221> NAME/KEY: misc_feature
<222> LOCATION: (13)..(13)
<223> OTHER INFORMATION: Xaa = Abu

<400> SEQUENCE: 21

Ala Asn Ala Ala Leu Lys Ala Gly Glu Leu Tyr Xaa Xaa Ile Leu Phe
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa = NMeAla
<220> FEATURE:
<221> NAME/KEY: misc_feature
<222> LOCATION: (13)..(13)
<223> OTHER INFORMATION: Xaa = Abu

<400> SEQUENCE: 22

Ala Asn Xaa Ala Leu Lys Ala Gly Glu Leu Tyr Lys Xaa Ile Leu Phe
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa = NMeAla
<220> FEATURE:
<221> NAME/KEY: misc_feature
<222> LOCATION: (12)..(12)
<223> OTHER INFORMATION: Xaa = NMeLys
<220> FEATURE:
<221> NAME/KEY: misc_feature
<222> LOCATION: (13)..(13)
<223> OTHER INFORMATION: Xaa = Abu

<400> SEQUENCE: 23

Ala Asn Xaa Ala Leu Lys Ala Gly Glu Leu Tyr Xaa Xaa Ile Leu Phe
1               5                   10                  15

<210> SEQ ID NO 24
<211> LENGTH: 16
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (12)..(12)
<223> OTHER INFORMATION: Xaa = NMeLys
<220> FEATURE:
<221> NAME/KEY: misc_feature
<222> LOCATION: (13)..(13)
<223> OTHER INFORMATION: Xaa = Abu

<400> SEQUENCE: 24

Ala Asn Ala Ala Leu Lys Ala Gly Glu Leu Tyr Xaa Xaa Ile Leu Tyr
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa = Abu

<400> SEQUENCE: 25

Tyr Leu Ile Xaa Lys Tyr Leu Glu Gly Ala Lys Leu Ala Ala Asn Ala
1               5                   10                  15

<210> SEQ ID NO 26
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 26

Xaa Val Trp Leu Trp Glu Asn Xaa
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 27

Xaa Val Trp Thr Leu Pro Asp Gln Xaa
1               5

<210> SEQ ID NO 28
<211> LENGTH: 29
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 28

Thr Gly Glu Leu Tyr Lys Xaa Ile Leu Tyr Thr Leu Ala Trp Lys Thr
1               5                   10                  15

Thr Ala Arg Leu Lys Glu Leu Asn Leu Val Tyr Thr Thr
            20                  25

<210> SEQ ID NO 29
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (15)..(15)
<223> OTHER INFORMATION: Xaa = Abu

<400> SEQUENCE: 29

Arg Arg Ala Asn Ala Ala Leu Lys Ala Gly Glu Leu Tyr Lys Xaa Ile
1               5                   10                  15

Leu Tyr

<210> SEQ ID NO 30
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 30

Arg Arg Ala Asn Ala Ala Leu Lys Ala Gly Glu Leu Tyr Lys Cys Ile
1               5                   10                  15

Leu Tyr

<210> SEQ ID NO 31
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 31

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln
            20                  25

<210> SEQ ID NO 32
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 32

Ala Leu Lys Ala Gly Glu Leu Tyr Lys
1               5
```

```
<210> SEQ ID NO 33
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 33

Met Ile Val Val Glu Leu Thr Asn Pro Leu Lys Ser Ser Gly Ile Glu
1               5                   10                  15

Asn Gly Ala Phe Gln Gly Met Lys Lys
            20                  25

<210> SEQ ID NO 34
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 34

Xaa Val Trp Leu Trp Glu Gln Xaa
1               5

<210> SEQ ID NO 35
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (13)..(13)
<223> OTHER INFORMATION: Xaa = Abu

<400> SEQUENCE: 35

Ala Asn Ala Ala Leu Lys Ala Gly Glu Leu Phe Lys Xaa Ile Leu Tyr
1               5                   10                  15
```

IMAGING AGENTS

CROSS-REFERENCE TO RELATED APPLICATIONS

This application is a filing under 35 U.S.C. 371 of international application number PCT/GB2007/001964, filed May 25, 2007, which claims priority to application number 0610395.6 filed May 25, 2006, in Great Britain the entire disclosure of which is hereby incorporated by reference.

TECHNICAL FIELD OF THE INVENTION

The present invention relates to diagnostic imaging and in particular to the diagnostic imaging of fibrosis. Diagnostic imaging agents are described which are suitable for this purpose, particularly for the diagnostic imaging of fibrosis in the liver, heart, kidneys and lungs.

DESCRIPTION OF RELATED ART

In simple terms, fibrosis is scar tissue and forms part of all "repair" processes in tissue. However, because of ongoing inflammation, infection and repeated injury, fibrosis scar tissue builds up and does not replace "functional" cells, thus leading to abnormal organ function and eventually organ failure. Fibrosis is one of the major, classic pathological processes in medicine. It is a key component of multiple diseases that affect millions of people worldwide and includes diseases such as:

a) Lung diseases such as idiopathic pulmonary fibrosis (lung fibrosis of unknown origin), asthma and chronic obstructive pulmonary disease.
b) Scleroderma: a heterogeneous and life threatening disease characterised by the excessive extracellular matrix deposition within connective tissue of the body (i.e. skin and visceral organs).
c) Post-surgical scarring following transplantation.
d) Diabetic retinopathy and age-related macular degeneration (AMD) (fibrotic diseases of the eye and leading causes of blindness).
e) Cardiovascular disease including atherosclerosis and vulnerable plaque.
f) Kidney fibrosis linked to diabetes—diabetic nephropathy and glomerulosclerosis.
g) IgA nephropathy (causes of kidney failure and the need for dialysis and retransplant).
h) Cirrhosis and biliary atresia (leading causes of liver fibrosis and failure).
i) Hepatitis C infection.
j) Rheumatoid arthritis.
k) Autoimmune diseases such as dermatomyositis.
l) Congestive heart failure.

The clinical manifestations of fibrosis vary widely. Taking the example of cirrhosis, the clinical manifestations vary from no symptoms at all, to liver failure, and are determined by both the nature and severity of the underlying liver disease as well as the extent of hepatic fibrosis. Up to 40% of patients with cirrhosis are asymptomatic and may remain so for more than a decade, but progressive deterioration is inevitable once complications develop including ascites, variceal hemorrhage or encephalopathy.

Fibrosis and cirrhosis therefore represent the consequences of a sustained wound healing response to chronic liver injury from a variety of causes including viral, autoimmune, drug-induced, cholestatic and metabolic diseases. The common causes of liver fibrosis and cirrhosis include immune-mediated damage, genetic abnormalities, and non-alcoholic steatohepatitis (NASH), which is particularly associated with diabetes and metabolic syndrome (MS). There is a high incidence of MS in the Western population. This syndrome typically occurs in individuals who are obese, have hyperlipidemia and hypertension, and often leads to the development of type II diabetes. The hepatic manifestation of metabolic syndrome is non-alcoholic fatty liver disease (NAFLD), with an estimated prevalence in the USA of 24% of the population. A fatty liver represents the less severe end of a spectrum of NAFLD that may progress to NASH and ultimately to cirrhosis of the liver. The development of fibrosis demonstrates a risk of such progression, and is presently assessed by means of a liver biopsy. However, liver biopsy causes significant discomfort, is not without risk and is costly. Furthermore, available blood tests for hepatic fibrosis are not reliable in NAFLD.

Fibrosis is characterized by the excessive secretion of extracellular matrix components.

This is caused by increased synthesis and decreased degradation of matrix proteins, most notably collagen types I and III. Types I and III collagen are major components of the extracellular matrix and are instrumental in the development of fibrosis. High levels of collagen III are observed in the early stages of the process of fibrosis, with collagen I subsequently becoming predominant. A number of groups have disclosed peptide compounds that bind to collagen. Chiang and Kang [J. Clin. Invest. 1997 100(8) 2079-84] and Chiang [Amer. J. Med. Sci. 2000 320(6) 362-67 and 2002 J. Biol. Chem. 277 34896-901] report synthetic peptides derived from the sequences of type I and III collagen receptors, which are found on platelets and inhibit collagen-mediated platelet aggregation and the release of ATP. Thomas et al [2005 J. Biol. Chem. 280(24) 22596-605] describe Endo180, a receptor which binds to the C-terminal region of type I collagen. Depraetera et al [1998 Blood 92(11) 4207] report two cyclic octapeptides that inhibited the binding Willebrand factor (vWF) to calfskin and human collagen type I. Tye et al [2005 J. Biol. Chem. 280(14) 13487-492] report the binding of synthetic peptide derived from recombinant bone sialoprotein (rBSP) to type I collagen.

WO 2006/054904 relates to contrast agents comprising targeting vectors that bind to areas of collagen formation. These contrast agents are suggested as being useful for diagnosis and monitoring of treatment of diseases related to the excessive formation of collagen, including, inter alia, fibrosis.

A need exists for further imaging agents for the detection of fibrosis.

SUMMARY OF THE INVENTION

The present invention provides a novel imaging agent suitable for the non-invasive visualization of fibrosis. A precursor for the preparation of the imaging agent is also provided by the invention, as well as a pharmaceutical composition comprising the imaging agent and a kit for the preparation of the pharmaceutical composition. In a further aspect, use of the imaging agent for in vivo imaging and in the preparation of a medicament for the diagnosis of a condition which comprises fibrosis is provided.

BRIEF DESCRIPTION OF THE DRAWINGS

FIG. 1 is a graph illustrating the binding of Imaging Agent 1 to a collagen type I coated plate over a range of concentrations of Imaging Agent 1.

DETAILED DESCRIPTION OF THE INVENTION

In a first aspect, the present invention provides an imaging agent comprising a collagen binding peptide (CBP) and an imaging moiety, wherein said CBP is selected from:
  (i) RRANAALKAGELYKXaaILY (SEQ ID NO. 14)
  (ii) GELYKXaaILY (SEQ ID NO. 15)
  (iii) DARKSEVQK (SEQ ID NO. 16)
  (iv) KELNVLYT (SEQ ID NO. 17)
  (v) XaaVWLWEQXaa (SEQ ID NO. 34)
  (vi) XaaVWLWENXaa (SEQ ID NO. 26)
  (vii) XaaVWTLPDQXaa (SEQ ID NO. 27),
  (viii) TGELYKXaaILYTLAWKTTARLKELNLVYTT (SEQ ID NO. 28)
  (ix) Saratin recombinant polypeptide derived from the saliva of the medicinal leech *Hirudo medicinalis*
  (x) Residues 176-201 of decorin
  (xi) Peptide analogues of any of peptides (i)-(x)

or said CBP is a stabilised, truncated and/or cyclic version of any of these peptides, or is a homo- or heterodimer of two of these peptides or truncated versions thereof, and where Xaa can be any of cysteine, 2-aminobutyric acid (Abu), methionine or alanine.

Each of the peptides (i)-(xi) above is or is derived from a fragment of a physiological peptide having collagen-binding activity. Preferably, the CBP is an 8-30-mer peptide, and most preferably an 8- to 20-mer peptide.

The imaging agent of the invention suitably binds to collagen with an affinity of less than 1 µM, preferably with an affinity less than 100 nM and most preferably with an affinity less than 10 nM.

The term "peptide analogue" in the context of peptide (xi) of the present invention means natural or synthetic peptides comprising all or part of peptides (i)-(x) in which one or more amino acid residues have been substituted with alternative amino acid residues, and which retains affinity for collagen. Preferred peptide analogues are synthetic peptides. With the aim of minimizing alteration of the peptide, it is common practice to substitute only a few amino acid residues and to make only conservative substitutions. The following table outlines substitutions that are regarded as conservative:

| Original aa residue | Exemplary substitutions |
| --- | --- |
| Ala | Ser |
| Arg | Lys |
| Asn | Gln, His |
| Asp | Glu |
| Cys | Ser, Met |
| Gln | Asn |
| Glu | Asp |
| Gly | Ala, Asn |
| His | Asn, Gln |
| Ile | Leu, Val |
| Leu | Ile, Val |
| Lys | Arg, Gln |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

However, any aa substitution is suitable as long as affinity for collagen is retained.

A "stabilised" version of the CBP of the present invention is a peptide of any of sequences (i)-(xi) that has been modified in order that the peptide has enhanced resistance to cleavage in plasma. It is important that the CBP remain intact in vivo so that its collagen-binding properties are retained and the imaging moiety is reliably delivered to the target.

One method to stabilise the CBP is to attach a $Z^1$ group to the N-terminus of the CBP, and/or to attach a $Z^2$ group to the C-terminus of the CBP. The $Z^1$ group substitutes the amine group of the last amino acid residue. Thus, when $Z^1$ is H, the amino terminus of the CBP terminates in a free $NH_2$ group of the last amino acid residue. The $Z^2$ group substitutes the carbonyl group of the last amino acid residue. Thus, when $Z^2$ is OH, the carboxy terminus of the CBP terminates in the free $CO_2H$ group of the last amino acid residue, and when $Z^2$ is $OB^c$ (where $B^c$ is a biocompatible cation) that terminal carboxy group is ionised as a $CO_2B^c$ group.

Suitable $Z^1$ groups for the CBP N-terminus are well-known to those skilled in the art and are suitably chosen from: N-acylated groups —NH(C=O)$R^G$ where the acyl group —(C=O)$R^G$ has $R^G$ chosen from: $C_{1-6}$ alkyl, $C_{3-10}$ aryl groups or comprises a polyethyleneglycol (PEG) building block. Preferred N-terminus groups are acetyl, benzyloxycarbonyl or trifluoroacetyl, most preferably acetyl.

Suitable $Z^2$ groups for the CBP C-terminus include: carboxamide, tert-butyl ester, benzyl ester, cyclohexyl ester, amino alcohol or a polyethyleneglycol (PEG) building block. Preferred such groups are carboxamide or PEG, most preferred such groups are carboxamide.

Additional examples of tactics to stabilise the CBP include: N-alkylation of amino acid residues, preferably N-methylation; acetylation of amino acid residues; incorporation of non-natural amino acids or amide bond isosteres; addition of other moieties not easily recognised by plasma enzymes, for example C-terminal extension with polyethylene glycol or diglycoloyl moieties; and, conversion of the peptide structure into its retro in-verso sequence, i.e. reversing the amino acid sequence and replacing all L-amino acids by D-amino acids.

A "truncated" version of the CBP of the present invention is a peptide of any of sequences (i)-(xi) wherein between 1 and 5 amino acids are absent from the carboxy and/or the amino terminus, with the proviso that said truncated version contains at least 5 amino acid residues.

A "cyclic" version of the CBP of the present invention is a CBP that has been cyclised by bridging using cysteine residues either present or added to the peptide sequence. Cyclisation can also be achieved by head-to-tail cyclisation, i.e. forming an amide bond between the N-terminal amino group and the C-terminal carboxy group. Where cysteine residues are added to the peptide sequence, they are preferably added to the terminal ends in order to achieve head-to-tail cyclisation. A further method to form a cyclic peptide is to form a bond between two amino acids through their side chains, for example a lysine and a glutamic acid.

CPB peptides may be obtained by conventional solid phase synthesis. Albericio provides a recent review of methodologies for solid phase peptide synthesis [Curr. Opinion Cell Biol. 2004 8 211-21].

Descriptions of the particular CPB peptides of the invention may be found in the following references (using the same numbering scheme as for peptides (i)-(x) above):
(i) Chiang and Kang 1997 J. Clin. Invest. 100(8) 2079-84
(ii) Chiang et al 2000 Am. J. Med. Sci. 320(6) 362-7
(iii) Chiang 2002 J. Biol. Chem. 277 34896-901
(iv) Chiang 2002 J. Biol. Chem. 277 34896-901
(v) Depraetere et al. 1998 Blood 92(11) 4207-11
(vi) Depraetere et al. 1998 Blood 92(11) 4207-11
(vii) Pareti et al 1987 J. Biol. Chem. 262(28) 13841
(viii) Zhu et al 2007 Thromb. Res. 119(1) 111-119

(ix) Cruz et al 2001 J. Vascular Surgery 34(4) 724-29
(x) Hunter et al 2001 J. Biomed. Mat. Res. 55(4) 496-502

By the term "imaging agent" is meant a compound designed to target a particular physiology or pathophysiology in a mammal, and which can be detected following its administration to the mammalian body in vivo.

In the imaging agent of the invention, the imaging moiety may be present as an integral part of the CBP, e.g. one of the atoms of the CBP could be $^{11}C$ instead of $^{12}C$. Alternatively, the imaging moiety may be conjugated to the CBP via a suitable chemical group, e.g. a metal chelate which can complex an imaging moiety which is a metal ion.

A linker may also be present linking the CBP to either the suitable chemical group or directly to the imaging moiety itself. Suitable linkers of the present invention are of Formula -(L)$_n$- wherein:
  each L is independently —CO—, —CR'$_2$—, —CR'=CR'—, C≡C, —CR'$_2$CO$_2$—, —CO$_2$CR'$_2$—, —NR'—, —NR'CO—, —CONR'—, —NR'(C=O)NR'—, —NR'(C=S)NR'—, —SO$_2$NR'—, —NR'SO$_2$—, —CR'$_2$OCR'$_2$—, —CR'$_2$SCR'$_2$—, —CR'$_2$NR'CR'$_2$—, a $C_{4-8}$ cycloheteroalkylene group, a $C_{4-8}$ cycloalkylene group, a $C_{5-12}$ arylene group, a $C_{3-12}$ heteroarylene group, an amino acid, a polyalkyleneglycol, polylactic acid or polyglycolic acid moiety;
  n is an integer of value 0 to 15;
  each R' group is independently H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl, or 2 or more R' groups, together with the atoms to which they are attached form a carbocyclic, heterocyclic, saturated or unsaturated ring.
with the proviso that said linker is not longer than a chain of 30 atoms.

It is envisaged that branched linker groups are also possible, i.e. a linker group -(L)$_n$-substituted with a further -(L)$_n$- linker group, which terminates with an R' group, as defined above. Such branched linkers are particularly useful in the context of manipulating the biodistribution and/or excretion of the imaging agent of the invention.

By the term "amino acid" is meant an L- or D-amino acid, amino acid analogue (e.g. napthylalanine) or amino acid mimetic which may be naturally occurring or of purely synthetic origin, and may be optically pure, i.e. a single enantiomer and hence chiral, or a mixture of enantiomers. Preferably the amino acids of the present invention are optically pure.

Such linkers also have application in relation to other aspects of the invention as described below. For the purpose of linking the CBP to either a suitable chemical group or directly to an imaging moiety, preferred L groups are —CO—, —CH$_2$—, —NH—, —NHCO—, —CONH—, —CH$_2$OCH$_2$—, and amino acids.

In a preferred embodiment, the CBP of the invention is selected from peptides (i)-(vii), listed above, or stabilised, truncated or cyclic versions thereof, or homo- or heterodimers of two of these peptides or truncated versions thereof, where Xaa is as previously defined.

In a most preferred embodiment, the CPB of the invention is selected from:
  (a) peptide (i) modified in one or more of the following ways:
    truncated to remove the 2 N-terminal arginines
    Xaa=2-aminobutyric acid or cysteine
    methylated alanine residues
    methylated lysine residues
    replacement of tyrosine is with lysine
    addition of polyethylene glycol chain and/or diglycolyl to the C-terminus;
  (b) peptide (i) modified as in (a), and converted to its retroinverso sequence;
  (c) peptide (ii) wherein Xaa=cysteine;
  (d) peptide (iii) unmodified or cyclised by means of 2 cysteine residues, one each added to the N- and C-termini;
  (e) peptide (iv) unmodified, or modified by either or both of the following ways:
    valine-5 and leucine-6 reversed
    cyclised by means of 2 cysteine residues, one each added to the N- and C-termini;
  (f) peptides (v)-(vii) wherein Xaa=cysteine;
  and wherein in each case the N-terminus is optionally protected with an acetyl and the C-terminus is optionally protected with an amide.

Examples of most preferred CPBs of the invention are as follows (all amino acids are L-amino acids unless otherwise stated):
  a) ANAALKAGELYKCILY-NH$_2$ (SEQ ID NO. 18)
  b) ANAALKAGELYK-[Abu]-ILY-NH$_2$ (SEQ ID NO. 19)
  c) Ac-ANAALKAGELFK-[Abu]-ILY-NH$_2$ (SEQ ID NO. 35)
  d) Ac-ANAALKAGELYK-[Abu]-ILF-NH$_2$ (SEQ ID NO. 20)
  e) Ac-ANAALKAGELY-[NMeLys]-[Abu]-ILF-NH$_2$ (SEQ ID NO. 21)
  f) Ac-AN-[NMeAla]-ALKAGELYK-[Abu]-ILF-NH$_2$ (SEQ ID NO. 22)
  g) Ac-AN-[NMeAla]-ALKAGELY-[NMeLys]-[Abu]-ILF-NH$_2$ (SEQ ID NO. 23)
  h) ANAALKAGELYK-[Abu]-ILY-[PEG(4)]-(diglycolyl)-NH$_2$ (SEQ ID NO. 19)
  i) ANAALKAGELY-[NMeLys]-[Abu]-ILY-[PEG(4)]-(diglycolyl)-NH$_2$ (SEQ ID NO. 24)
  j) ANAALKAGELYK-[Abu]-ILY-[PEG(4)]-(diglycolyl)-COOH (SEQ ID NO. 19)
  k) D-YLI-[Abu]-KYLEGAKLAANA-NH$_2$ (SEQ ID NO. 25)
  l) GELYKCILY-NH$_2$ (SEQ ID NO. 5)
  m) DARKSEVQK-NH$_2$ (SEQ ID NO. 16)
  n) CDARKSEVQKC-NH$_2$ (SEQ ID NO. 6) cyclised via two added terminal cysteine residues
  o) KELNVLYT-NH$_2$ (SEQ ID NO. 17)
  p) KELNLVYT-NH$_2$ (SEQ ID NO. 7)
  q) Ac-KELNLVYT-NH$_2$ (SEQ ID NO. 7)
  r) Ac-CKELNLVYTC-NH$_2$ (SEQ ID NO. 9) cyclised by bridging two added terminal cysteine residues
  s) CVWLWEQC-NH$_2$ (SEQ ID NO. 10) cyclised by bridging cysteine residues
  t) CVWLWENC-NH$_2$ (SEQ ID NO. 11) cyclised by bridging cysteine residues
  u) CVWTLPDQC-NH$_2$ (SEQ ID NO. 12) cyclised by bridging cysteine residues
  In the above list, "Ac" is an acetyl group, "Abu" is 2-aminobutyric acid, "NMeLys" is N-methylated lysine, "NMeAla" is N-methylated alanine, and "PEG(X)" is a polyethylene glycol chain of X units.

In a most preferred embodiment, the CBP of the invention is a peptide selected from (i)-(iv) listed above, or stabilised, truncated or cyclic versions thereof, or homo- or heterodimers of two of these peptides or truncated versions thereof, where Xaa is as previously defined.

The "imaging moiety" may be detected either externally to the human body or via use of detectors designed for use in vivo, such as intravascular radiation or optical detectors such as endoscopes, or radiation detectors designed for intra-operative use. The imaging moiety is preferably chosen from:
 (i) a radioactive metal ion;
 (ii) a paramagnetic metal ion;
 (iii) a gamma-emitting radioactive halogen;
 (iv) a positron-emitting radioactive non-metal;
 (v) a hyperpolarised NMR-active nucleus; and,
 (vi) a reporter suitable for in vivo optical imaging.

When the imaging moiety is a radioactive metal ion, i.e. a radiometal, suitable radiometals can be either positron emitters such as $^{64}$Cu, $^{48}$V, $^{52}$Fe, $^{55}$Co, $^{94m}$Tc or $^{68}$Ga; or γ-emitters such as $^{99m}$Tc, $^{111}$In, $^{113}$In, or $^{67}$Ga. Preferred radiometals are $^{99m}$Tc, $^{64}$Cu, $^{68}$Ga and $^{111}$In. Most preferred radiometals are γ-emitters, especially $^{99m}$Tc.

When the imaging moiety is a paramagnetic metal ion, suitable such metal ions include: Gd(III), Mn(II), Cu(II), Cr(III), Fe(III), Co(II), Er(II), Ni(II), Eu(III) or Dy(III). Preferred paramagnetic metal ions are Gd(III), Mn(II) and Fe(III), with Gd(III) being especially preferred.

When the imaging moiety is a gamma-emitting radioactive halogen, the radiohalogen is suitably chosen from $^{123}$I, $^{131}$I or $^{77}$Br. $^{125}$I is specifically excluded as it is not suitable for use as an imaging moiety for in vivo diagnostic imaging. A preferred gamma-emitting radioactive halogen is $^{123}$I.

When the imaging moiety is a positron-emitting radioactive non-metal, suitable such positron emitters include: $^{11}$C, $^{13}$N, $^{15}$O, $^{17}$F, $^{18}$F, $^{75}$Br, $^{76}$Br or $^{124}$I. Preferred positron-emitting radioactive non-metals are $^{11}$C, $^{13}$N, $^{18}$F and $^{124}$I, especially $^{11}$C and $^{18}$F, most especially $^{18}$F.

When the imaging moiety is a hyperpolarised NMR-active nucleus, such NMR-active nuclei have a non-zero nuclear spin, and include $^{13}$C, $^{15}$N, $^{19}$F, $^{29}$Si and $^{31}$P. Of these, $^{13}$C is preferred. By the term "hyperpolarised" is meant enhancement of the degree of polarisation of the NMR-active nucleus over its' equilibrium polarisation. The natural abundance of $^{13}$C (relative to $^{12}$C) is about 1%, and suitable $^{13}$C-labelled compounds are suitably enriched to an abundance of at least 5%, preferably at least 50%, most preferably at least 90% before being hyperpolarised. At least one carbon atom of the imaging agent of the invention is suitably enriched with $^{13}$C, which is subsequently hyperpolarised.

When the imaging moiety is a reporter suitable for in vivo optical imaging, the reporter is any moiety capable of detection either directly or indirectly in an optical imaging procedure. The reporter might be a light scatterer (e.g. a coloured or uncoloured particle), a light absorber or a light emitter. More preferably the reporter is a dye such as a chromophore or a fluorescent compound. The dye can be any dye that interacts with light in the electromagnetic spectrum with wavelengths from the ultraviolet light to the near infrared. Most preferably the reporter has fluorescent properties.

Preferred organic chromophoric and fluorophoric reporters include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots).

Particular examples of chromophores which may be used include: fluorescein, sulforhodamine 101 (Texas Red), rhodamine B, rhodamine 6G, rhodamine 19, indocyanine green, Cy2, Cy3, Cy3B, Cy3.5, Cy5, Cy5.5, Cy7, Cy7.5, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750.

Particularly preferred are dyes which have absorption maxima in the visible or near infrared (NIR) region, between 400 nm and 3 μm, particularly between 600 and 1300 nm. Optical imaging modalities and measurement techniques include, but not limited to: luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; interferometry; coherence interferometry; diffuse optical tomography and fluorescence mediated diffuse optical tomography (continuous wave, time domain and frequency domain systems), and measurement of light scattering, absorption, polarisation, luminescence, fluorescence lifetime, quantum yield, and quenching.

Preferred imaging moieties are those which can be detected externally in a non-invasive manner following administration in vivo, such as by means of SPECT, PET and MR. Most preferred imaging moieties are radioactive, especially radioactive metal ions, gamma-emitting radioactive halogens and positron-emitting radioactive non-metals, particularly those suitable for imaging using SPECT or PET. For some applications, however, other imaging moieties are preferred, e.g. for imaging AMD optical imaging moieties are preferred.

Preferred imaging agents of the invention do not undergo facile metabolism in vivo, and hence most preferably exhibit a half-life in vivo of 60 to 240 minutes in humans. The imaging agent is preferably excreted via the kidney (i.e. exhibits urinary excretion). The imaging agent preferably exhibits a signal-to-background ratio at diseased foci of at least 1.5, most preferably at least 5, with at least 10 being especially preferred. Where the imaging agent comprises a radioisotope, clearance of one half of the peak level of imaging agent which is either non-specifically bound or free in vivo, preferably occurs over a time period less than or equal to the radioactive decay half-life of the radioisotope of the imaging moiety.

Furthermore, the molecular weight of the imaging agent is suitably up to 5000 Daltons.

Preferably, the molecular weight is in the range 150 to 3000 Daltons, most preferably 200 to 1500 Daltons, with 300 to 800 Daltons being especially preferred.

Suitably, the imaging moiety is conjugated to the CBP via either its N- or C-terminus, or via any of the amino acid side chains. Preferably, the imaging moiety is conjugated to the CBP via either the N- or C-terminus of the CBP, optionally via a linker of Formula -(L)$_n$- as described above and preferably a PEG linker.

Examples of preferred imaging agents of the invention are illustrated below:

| # | Imaging Agent |
|---|---|
| 1 | [$^{99m}$Tc-Chelate II]-ANAALKAGELYKCILY-NH$_2$ (SEQ ID NO. 18) |
| 2 | [$^{99m}$Tc-Chelate II]-[PEG(12)]-ANAALKAGELYKCILY-NH$_2$ (SEQ ID NO. 18) |
| 3 | [$^{99m}$Tc-Chelate II]-DARKSEVQK-NH$_2$ (SEQ ID NO. 16) |
| 4 | [$^{99m}$Tc-Chelate II]-GELYKCILY (SEQ ID NO. 5) |
| 5 | [$^{99m}$Tc-Chelate II]-[PEG(12)]-GELYKCILY (SEQ ID NO. 5) |
| 6 | [$^{99m}$Tc-Chelate II]-RRANAALKAGELYK-[Abu]-ILY (SEQ ID NO. 29) |
| 7 | [$^{99m}$Tc-Chelate II]-CDARKSEVQKC (SEQ ID NO. 6) [cyclised via terminal Cys residues] |
| 8 | [$^{99m}$Tc-Chelate II]-KELNLVYT (SEQ ID NO. 7) |
| 9 | [$^{99m}$Tc-Chelate II]-CVWLWENC (SEQ ID NO. 11) [cyclised via terminal Cys residues] |
| 10 | [$^{99m}$Tc-Chelate II]-CVWLWEQC-NH$_2$ (SEQ ID NO. 10) [cyclised via terminal Cys residues] |
| 11 | [$^{99m}$TC-Chelate II]-CVWTLPDQC (SEQ ID NO. 12) [cyclised via terminal Cys residues] |
| 12 | [$^{99m}$Tc-Chelate II]-NGVFKYRPRYFLYKHAYFYPPLKRFPVQ (SEQ ID NO. 31) |
| 13 | [$^{99m}$Tc-Chelate I]-ANAALKAGELYKCILY-NH$_2$ (SEQ ID NO. 18) |
| 14 | [$^{99m}$Tc-Chelate I]-[PEG(12)]-ANAALKAGELYKCILY-NH$_2$ (SEQ ID NO. 18) |
| 15 | [$^{99m}$Tc-Chelate I]-DARKSEVQK-NH$_2$ (SEQ ID NO. 16) |
| 16 | [$^{99m}$Tc-Chelate I]-GELYKCILY (SEQ ID NO. 5) |
| 17 | [$^{99m}$Tc-Chelate I]-[PEG(12)]-GELYKCILY (SEQ ID NO. 5) |
| 18 | [$^{99m}$Tc-Chelate I]-RRANAALKAGELYK-[Abu]-ILY (SEQ ID NO. 29) |
| 19 | [$^{99m}$Tc-Chelate I]-CDARKSEVQKC (SEQ ID NO. 6) [cyclised via terminal Cys residues] |
| 20 | [$^{99m}$Tc-Chelate I]-KELNLVYT (SEQ ID NO. 7) |
| 21 | [$^{99m}$Tc-Chelate I]-CVWLWENC (SEQ ID NO. 11) [cyclised via terminal Cys residues] |
| 22 | [$^{99m}$Tc-Chelate I]-CVWLWEQC (SEQ ID NO. 10) [cyclised via terminal Cys residues] |
| 23 | [$^{99m}$Tc-Chelate I]-CVWTLPDQC (SEQ ID NO. 12) [cyclised via terminal Cys residues] |
| 24 | [$^{99m}$Tc-Chelate I]-NGVFKYRPRYFLYKHAYFYPPLKRFPVQ (SEQ ID NO. 31) |
| 25 | $^{123}$I-labelled RRANAALKAGELYKCILY (SEQ ID NO. 30) |
| 26 | $^{123}$I-labelled ALKAGELYK (SEQ ID NO. 32) |
| 27 | $^{123}$I-labelled GELYKCILY (SEQ ID NO. 5) |
| 28 | $^{123}$I-labelled ANAALKAGELYKCILY-NH$_2$ (SEQ ID NO. 18) |
| 29 | $^{123}$I-labelled Ac-KELNLVYT-NH$_2$ (SEQ ID NO. 7) |
| 30 | $^{18}$F-labelled RRANAALKAGELYKCILY (SEQ ID NO. 30) |
| 31 | $^{18}$F-labelled ALKAGELYK (SEQ ID NO. 32) |
| 32 | $^{18}$F-labelled GELYKCILY (SEQ ID NO. 5) |
| 33 | $^{18}$F-labelled ANAALKAGELYKCILY-NH$_2$ (SEQ ID NO. 18) |
| 34 | $^{18}$F-labelled KELNLVYT-NH$_2$ (SEQ ID NO. 7) |
| 35 | $^{123}$I-labelled KELNLVYT-NH$_2$ (SEQ ID NO. 17) |
| 36 | $^{123}$I-labelled Ac-CKELNVLYTC-NH$_2$ (SEQ ID NO. 9) [cyclised via terminal Cys residues] |
| 37 | $^{123}$I-labelled Ac-Y-[PEG(4)]-DARKSEVQK (SEQ ID NO. 16) |
| 38 | $^{99m}$Tc(CO)$_3$-[α-His]-[Ac]-ANAALKAGELYK[Abu]ILY (SEQ ID NO. 19) |
| 39 | $^{99m}$Tc-HYNIC-ANAALKAGELYK[Abu]ILY (SEQ ID NO. 19) |
| 40 | $^{99m}$Tc-Chelate I-ANAALKAGELYK[Abu]ILY (SEQ ID NO. 19) |
| 41 | $^{99m}$Tc-Chelate II-MIVVELTNPLKSSGIENGAFQGMKK (SEQ ID NO. 33) |
| 42 | $^{99m}$Tc-Chelate I-ANAALKAGELYK[Abu]ILY-[PEG(4)]-[diglycoloyl]-NH$_2$ (SEQ ID NO. 19) |
| 43 | $^{99m}$Tc-Chelate I-ANAALKAGELY-[NMeLys]-[Abu]-ILY-[PEG(4)]-[diglycoloyl]-NH$_2$ (SEQ ID NO. 24) | wherein Ac, Abu, NMeLys and PEG(X) are as previously defined, and α-His is α-histidine.

Using an in vitro assay (described in Example 18), affinity for collagen for a number of these preferred imaging agents was demonstrated to be in the nanomolar range, in some cases less than 50 nM.

Chelate I and Chelate II are described in more detail below in relation to the second aspect of the invention. For Imaging Agents 1-12 above, the point of attachment to Chelate II is at the bridgehead group (see Formula Ib below). For imaging agents 13-24 above, the point of attachment to Chelate I is at the bridgehead group (see Formula IIa below).

For Imaging Agents 25 and 28 above, $^{123}$I is attached to the phenol side chain of the tyrosine residue closest to the N-terminus. Imaging Agents 25a and 28a can also be envisaged whereby the $^{123}$I is attached to the phenol side chain of the alternative tyrosine residue. For compounds 26, 27 and 29, $^{123}$I is attached to the phenol side chain of the tyrosine residue.

For Imaging Agents 30-34 above, $^{18}$F is attached to the N-terminus of the CBP via thiol coupling, i.e.:

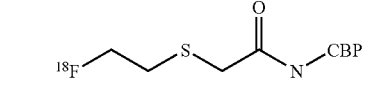

wherein CBP represents the particular peptide in question. For more detail on this type of $^{18}$F-labelled imaging agent, see description below in relation to Formulae III, IIIa and IIIb.

Synthesis of the imaging agents via precursor compounds is described in more detail below in relation to the second aspect of the invention.

Analysis of Imaging Agents 1, 29, 35, and 36 has demonstrated that they bind with high affinity to collagen in vitro. Imaging Agent 1 has been demonstrated to have favourable biodistribution characteristics as a liver fibrosis imaging agent (see Example 19). In a rat model of liver fibrosis (bile-duct ligation; BDL—described in Example 20), it was seen that the activity administered as Imaging Agent 1 is rapidly removed from the blood pool and significant accumulation was observed in the liver of BDL animals compared to sham animals at 1 and 2 hours post injection.

In a second aspect, the present invention provides a precursor for the preparation of the imaging agent of the invention comprising a CBP as described above and a chemical group capable of reacting with a source of an imaging moiety, wherein said chemical group comprises:
(i) a synthetic ligand capable of complexing a metallic imaging moiety;
(ii) an organometallic derivative such as a trialkylstannane or a trialkylsilane;
(iii) a derivative containing an alkyl halide, alkyl tosylate or alkyl mesylate for nucleophilic substitution;
(iv) a derivative which alkylates thiol-containing compounds to give a thioether-containing product, and wherein said chemical group is either an integral part of said CBP or is conjugated to said CBP.

A "precursor" comprises a derivative of the CBP of the invention, designed so that chemical reaction with a convenient chemical form of the imaging moiety occurs site-specifically; can be conducted in a minimal number of steps (ideally a single step); and without the need for significant purification (ideally no further purification), to give the desired imaging agent. Such precursors are synthetic and can conveniently be obtained in good chemical purity. The "precursor" may optionally comprise one or more protecting groups for certain functional groups of the CBP.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Protecting groups are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tert-butyl; alkoxymethyl or alkoxyethyl; benzyl; acetyl; benzoyl; trityl (Trt) or trialkylsilyl such as tetrabutyldimethylsilyl. For thiol groups, suitable protecting groups are: trityl and 4-methoxybenzyl. The use of further protecting groups are described in 'Protective Groups in Organic Synthesis', Theorodora W. Greene and Peter G. M. Wuts, (Third Edition, John Wiley & Sons, 1999).

Preferably, said chemical group capable of reacting with a source of an imaging moiety comprises:
  (i) a synthetic ligand capable of complexing a metallic imaging moiety; or,
  (ii) an organometallic derivative such as a trialkylstannane or a trialkylsilane.

When the radioisotope is a radioactive metal ion, the radiopharmaceutical preferably comprises a metal complex of the radioactive metal ion with a synthetic ligand. By the term "metal complex" is meant a coordination complex of the metal ion with one or more ligands. It is strongly preferred that the metal complex is "resistant to transchelation", i.e. does not readily undergo ligand exchange with other potentially competing ligands for the metal coordination sites. Potentially competing ligands include other excipients in the preparation in vitro (e.g. radioprotectants or antimicrobial preservatives used in the preparation), or endogenous compounds in vivo (eg. glutathione, transferrin or plasma proteins). The term "synthetic" has its conventional meaning, i.e. man-made as opposed to being isolated from natural sources e.g. from the mammalian body. Such compounds have the advantage that their manufacture and impurity profile can be fully controlled.

Suitable ligands for use in the present invention which form metal complexes resistant to transchelation include: chelating agents, where 2-6, preferably 2-4, metal donor atoms are arranged such that 5- or 6-membered chelate rings result (by having a non-coordinating backbone of either carbon atoms or non-coordinating heteroatoms linking the metal donor atoms); or monodentate ligands which comprise donor atoms which bind strongly to the metal ion, such as isonitriles, phosphines or diazenides. Examples of donor atom types which bind well to metals as part of chelating agents are: amines, thiols, amides, oximes, and phosphines. Phosphines form such strong metal complexes that even monodentate or bidentate phosphines form suitable metal complexes. The linear geometry of isonitriles and diazenides is such that they do not lend themselves readily to incorporation into chelating agents, and are hence typically used as monodentate ligands. Examples of suitable isonitriles include simple alkyl isonitriles such as tert-butylisonitrile, and ether-substituted isonitriles such as MIBI (i.e. 1-isocyano-2-methoxy-2-methylpropane). Examples of suitable phosphines include Tetrofosmin, and monodentate phosphines such as tris(3-methoxypropyl) phosphine. Examples of suitable diazenides include the HYNIC series of ligands i.e. hydrazine-substituted pyridines or nicotinamides.

Examples of suitable chelating agents for technetium which form metal complexes resistant to transchelation include, but are not limited to:
  (i) diaminedioximes;
  (ii) $N_3S$ ligands having a thioltriamide donor set such as MAG3 (mercaptoacetyltriglycine) and related ligands; or having a diamidepyridinethiol donor set such as Pica;
  (iii) $N_2S_2$ ligands having a diaminedithiol donor set such as BAT or ECD (i.e. ethylcysteinate dimer), or an amideaminedithiol donor set such as MAMA;
  (iv) $N_4$ ligands which are open chain or macrocyclic ligands having a tetramine, amidetriamine or diamidediamine donor set, such as cyclam, monoxocyclam dioxocyclam;
  (v) $N_2O_2$ ligands having a diaminediphenol donor set;
  (vi) α-histidine+$Tc(CO)_3$ Preferred chelating agents of the invention for technetium are diaminedioximes and tetraamines, and α-histidine+$Tc(CO)_3$. In an alternative preferred embodiment, a HYNIC ligand is used in the formation of a technetium complex. Preferred versions are now described in more detail.

Preferred diaminedioximes are of Formula (I):

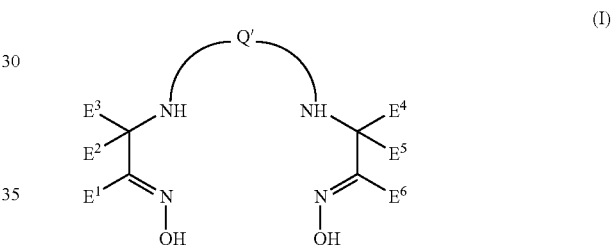

where $E^1$-$E^6$ are each independently an R* group;
each R* is H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl, $C_{2-10}$ carboxyalkyl or $C_{1-10}$ aminoalkyl, or two or more R* groups together with the atoms to which they are attached form a carbocyclic, heterocyclic, saturated or unsaturated ring, and wherein one or more of the R* groups is conjugated to the CBP;
and Q' is a bridging group of formula $-(J')_e-$;
where e is 3, 4 or 5 and each J' is independently —O—, —NR*— or —C(R*)$_2$— provided that $-(J')_e-$ contains a maximum of one J' group which is —O— or —NR*—.

Preferred Q' groups are as follows:
Q'=—($CH_2$)(CHR*)($CH_2$)— i.e. propyleneamine oxime or PnAO derivatives;
Q'=—($CH_2$)$_2$(CHR*)($CH_2$)$_2$— i.e. pentyleneamine oxime or PentAO derivatives;
Q'=—($CH_2$)$_2$NR*($CH_2$)$_2$—.

$E^1$ to $E^6$ are preferably chosen from: $C_{1-3}$ alkyl, alkylaryl alkoxyalkyl, hydroxyalkyl, fluoroalkyl, carboxyalkyl or aminoalkyl. Most preferably, each $E^1$ to $E^6$ group is $CH_3$.

Conjugation of a CBP to Formula I forms a precursor compound. The CBP is preferably conjugated at either the $E^1$ or $E^6$ R* group, or an R* group of the Q' moiety. Most preferably, it is conjugated to an R* group of the Q' moiety. When it is conjugated to an R* group of the Q' moiety, the R* group is preferably at the bridgehead position. In that case, Q' is preferably —($CH_2$)(CHR*)($CH_2$)—, —($CH_2$)$_2$(CHR*)

—(CH$_2$)$_2$— or —(CH$_2$)$_2$NR*(CH$_2$)$_2$—, most preferably —(CH$_2$)$_2$(CHR*)(CH$_2$)$_2$—. An especially preferred diaminedioxime precursor compound has the Formula (Ia):

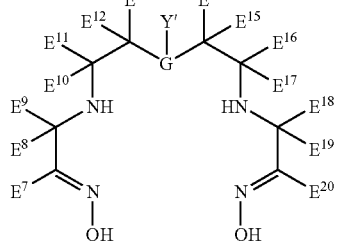

where:
E$^7$-E$^{20}$ are each independently an R* group;
G is N or CR*;
Y' is -(L)$_n$-CBP, wherein -(L)$_n$- is a linker group as previously defined, and CBP is as previously defined.

A preferred chelator of Formula (Ia) is of Formula (Ib):

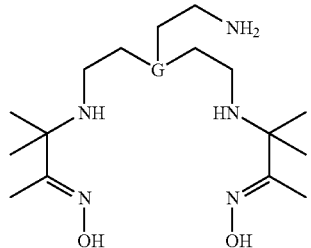

where G is as defined above, and is preferably CH (Chelate I; synthesis described in Example 1);
such that the CBP is conjugated via the bridgehead —CH$_2$CH$_2$NH$_2$ group to form a precursor compound.

Preferred precursor compounds formed with tetraamine chelators are of Formula II:

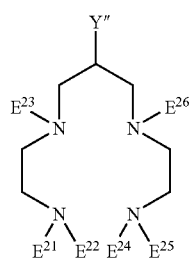

wherein:
Y'' is -(L)$_n$-CPB, wherein -(L)$_n$- is a linker group as previously defined and CBP is as previously defined. Preferably for Y'', -(L)$_n$- does not contain aryl rings, helping to minimize the lipophilicity of the complex.
E$^{21}$ to E$^{26}$ are R* groups as previously defined.

A most preferred precursor compound formed with a tetraamine chelate is of Formula IIa:

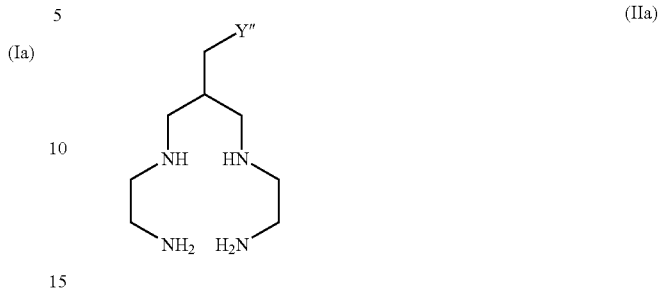

wherein Y'' is as defined above.

An especially preferred precursor compound formed with a tetraamine chelate is of Formula IIa wherein Y'' is —CO-CBP (Chelate II-CBP), wherein CBP is as previously defined.

In another preferred embodiment, the CPB of the invention may be labelled with $^{99m}$Tc by the preparation of a precursor which is a conjugate of the CPB and 6-hydrazinonicotinamide (HYNIC) of Formula III:

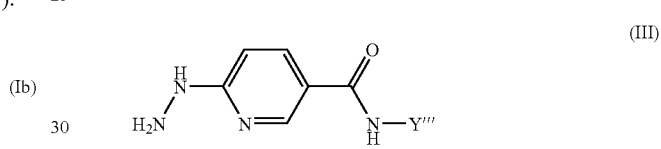

wherein Y'''-(L)$_n$-CPB, wherein -(L)$_n$- is a linker group as previously defined and CPB is as previously defined.

Since HYNIC can only occupy two coordination sites, a coligand is required in order to complete the coordination sphere of $^{99m}$Tc. Suitable coligands include tricine, or tricine plus a second phosphine or pyridine coligand. Examples of phosphine coligands include trisodium triphenylphosphine-3,3',3''-trisulfonate (TPPTS), disodium triphenylphosphine-3,3'-disulfonate (TPPDS) and sodium triphenylphosphone-3-monosulfonate (TPPMS). Examples of pyridine coligands include nicotinic acid (NIC), isonicotinic acid (ISONIC), 2-(4-pyridyl)ethylsulfonic acid (PES) and pyridine-3-sulfonic acid. Preferably, $^{99m}$Tc labelling of precursors of Formula III is carried out where the coligand is tricine, or is a combination of tricine plus TPPTS.

A thorough review of radiolabelling techniques involving HYNIC is given by Liu [Top Curr. Chem. 2005 252 pp 117-153].

In a yet further preferred embodiment, the CPB of the invention may additionally be labelled with $^{99m}$Tc by means of a precursor in which a histidine residue is added to the N-terminus of the CPB, preferably via an acetyl linker. There are alternative ways by which the histidine can be linked to the CPB to form a precursor suitable for $^{99m}$Tc labelling:

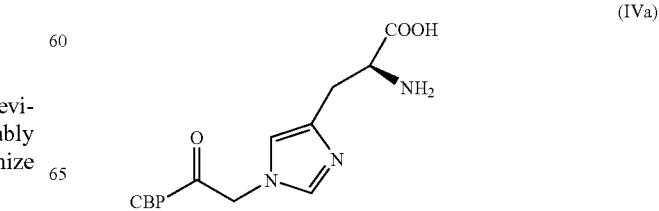

-continued

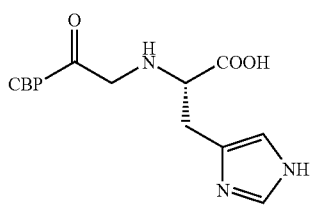
(IVb)

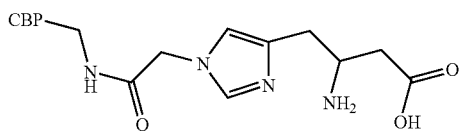
(IVc)

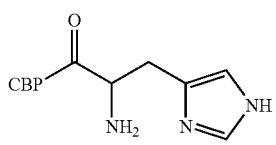
(IVd)

wherein CPB is a CPB of the invention as previously defined.

Depending on how it is conjugated, histidine provides either two or three coordination sites which can react with [$^{99m}$Tc(OH$_2$)$_3$—(CO)$_3$]$^+$ in a facial geometry to form an imaging agent of the invention. Preferred conjugates provide three coordination sites, i.e. Formulas IVa-c above.

Methods to prepare such precursor and imaging agent compounds are detailed by Banerjee et al [Nuc. Med. Biol. 2005 32 pp 1-20] and by Pak et al [Chem. Eur. J. 2003 9 pp 2053-2061].

The above described ligands are particularly suitable for complexing technetium e.g. $^{94m}$Tc or $^{99m}$Tc, and are described more fully by Jurisson et al [Chem. Rev., 99, 2205-2218 (1999)]. The ligands are also useful for other metals, such as copper ($^{64}$Cu or $^{67}$Cu), vanadium (e.g. $^{48}$V), iron (eg. $^{52}$Fe), or cobalt (e.g. $^{55}$Co).

Other suitable ligands are described in Sandoz WO 91/01144, which includes ligands which are particularly suitable for indium, yttrium and gadolinium, especially macrocyclic aminocarboxylate and aminophosphonic acid ligands. Ligands which form non-ionic (i.e. neutral) metal complexes of gadolinium are known and are described in U.S. Pat. No. 4,885,363. Particularly preferred for gadolinium are chelates including DTPA, ethylene diamine tetraacetic acid (EDTA), triethylene tetraamine hexaacetic acid (TTHA), 1,4,7,10-tetraazacyclododecane-1,4,7,10-tetraacetic acid (DOTA), 10-(2-hydroxypropyl)-1,4,7,10-tetraazacyclododecane-1,4,7-triacetic acid (DO3A) and derivatives of these.

It is envisaged that the role of the linker group -(L)$_n$- is to distance the relatively bulky technetium complex, which results upon metal coordination, from the active site of the CBP so that e.g. substrate binding is not impaired. This can be achieved by a combination of flexibility (e.g. simple alkyl chains), so that the bulky group has the freedom to position itself away from the active site and/or rigidity such as a cycloalkyl or aryl spacer which orientates the metal complex away from the active site. The nature of the linker group can also be used to modify the biodistribution of the resulting technetium complex of the conjugate. Thus, e.g. the introduction of ether groups in the linker will help to minimise plasma protein binding, or the use of polymeric linker groups such as polyalkyleneglycol, especially polyethyleneglycol (PEG) can help to prolong the lifetime of the agent in the blood in vivo.

Preferred linker groups -(L)$_n$- in the context of these chelators have a backbone chain (i.e. the linked atoms which make up the -(L)$_n$- moiety) which contains 2 to 10 atoms, most preferably 2 to 5 atoms, with 2 or 3 atoms being especially preferred. A minimum linker group backbone chain of 2 atoms confers the advantage that the chelator is well-separated from the biological targeting moiety so that any interaction is minimised. Furthermore, the CBP is unlikely to compete effectively with the coordination of the chelator to the metal ion. In this way, both the biological targeting characteristics of the CBP, and the metal complexing capability of the chelator is maintained. It is strongly preferred that the CBP is bound to the chelator in such a way that the linkage does not undergo facile metabolism in blood. That is because such metabolism would result in the imaging metal complex being cleaved off before the labelled CBP reaches the desired in vivo target site. The CBP is therefore preferably covalently bound to the metal complexes of the present invention via -(L)$_n$- linker groups which are not readily metabolised. Suitable such linkages are carbon-carbon bonds, amide bonds, urea or thiourea linkages, or ether bonds.

Non-peptide linker groups such as alkylene groups or arylene groups have the advantage that there are no significant hydrogen bonding interactions with the conjugated CBP so that the linker does not wrap round onto the CBP. Preferred alkylene spacer groups are —(CH$_2$)$_q$— where q is an integer of value 2 to 5. Preferably q is 2 or 3. Preferred arylene spacers are of formula:

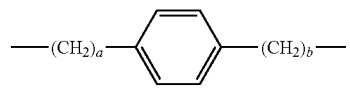

where: a and b are each independently 0, 1 or 2.

A preferred Y' or Y" group is thus —CH$_2$CH$_2$-(L)$_p$-CBP,— where p is an integer of value 0 to 3. Most preferably, -(L)$_p$- is —CO— or —NR—. For Formula I, when G is N and -(L)$_p$- is —NH—, this grouping has the additional advantage that it stems from the symmetrical intermediate N(CH$_2$CH$_2$NH$_2$)$_3$, which is commercially available.

When the imaging metal is technetium, the usual technetium starting material is pertechnetate, i.e. TcO$_4^-$ which is technetium in the Tc(VII) oxidation state. Pertechnetate itself does not readily form metal complexes, hence the preparation of technetium complexes usually requires the addition of a suitable reducing agent such as stannous ion to facilitate complexation by reducing the oxidation state of the technetium to the lower oxidation states, usually Tc(I) to Tc(V). The solvent may be organic or aqueous, or mixtures thereof. When the solvent comprises an organic solvent, the organic solvent is preferably a biocompatible solvent, such as ethanol or DMSO. Preferably the solvent is aqueous, and is most preferably isotonic saline.

Where the imaging moiety is radioiodine, preferred precursors are those which comprise a derivative which either undergoes electrophilic or nucleophilic iodination or undergoes condensation with a labelled aldehyde or ketone. Examples of the first category are:
 (a) organometallic derivatives such as a trialkylstannane (eg. trimethylstannyl or tributylstannyl), or a trialkylsilane (eg. trimethylsilyl) or an organoboron compound (e.g. boronate esters or organotrifluoroborates);
 (b) a non-radioactive alkyl bromide for halogen exchange or alkyl tosylate, mesylate or triflate for nucleophilic iodination;

(c) aromatic rings activated towards nucleophilic iodination (eg. aryl iodonium salt aryl diazonium, aryl trialkylammonium salts or nitroaryl derivatives).

The precursor preferably comprises: a non-radioactive halogen atom such as an aryl iodide or bromide (to permit radioiodine exchange); an organometallic precursor compound (e.g. trialkyltin, trialkylsilyl or organoboron compound); or an organic precursor such as triazenes or a good leaving group for nucleophilic substitution such as an iodonium salt. Preferably for radioiodination, the precursor comprises an organometallic precursor compound, most preferably trialkyltin.

Precursors and methods of introducing radioiodine into organic molecules are described by Bolton [J. Lab. Comp. Radiopharm., 45, 485-528 (2002)]. Suitable boronate ester organoboron compounds and their preparation are described by Kabalka et al [Nucl. Med. Biol., 29, 841-843 (2002) and 30, 369-373 (2003)]. Suitable organotrifluoroborates and their preparation are described by Kabalka et al [Nucl. Med. Biol., 31, 935-938 (2004)].

Examples of aryl groups to which radioactive iodine can be attached are given below:

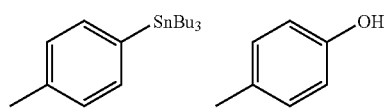

Both contain substituents which permit facile radioiodine substitution onto the aromatic ring. Where there are tyrosine residues already present in the CBP peptide sequence, radioiodination can be carried out using the inherent phenol group. In an alternative strategy, a tyrosine residue may be added to the peptide sequence for radioiodination, as long as the collagen-binding characteristics are not impaired.

Alternative substituents containing radioactive iodine can be synthesised by direct iodination via radiohalogen exchange, e.g.

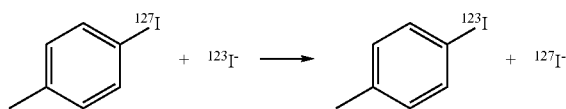

The radioiodine atom is preferably attached via a direct covalent bond to an aromatic ring such as a benzene ring, or a vinyl group since it is known that iodine atoms bound to saturated aliphatic systems are prone to in vivo metabolism and hence loss of the radioiodine.

Radiofluorination may be carried out via direct labelling using the reaction of $^{18}$F-fluoride with a suitable chemical group in the precursor having a good leaving group, such as an alkyl bromide, alkyl mesylate or alkyl tosylate. $^{18}$F can also be introduced by alkylation of N-haloacetyl groups with a $^{18}$F(CH$_2$)$_3$OH reactant, to give —NH(CO)CH$_2$O(CH$_2$)$_3$$^{18}$F derivatives. For aryl systems, $^{18}$F-fluoride nucleophilic displacement from an aryl diazonium salt, aryl nitro compound or an aryl quaternary ammonium salt are suitable routes to aryl-$^{18}$F derivatives.

A $^{18}$F-labelled compound of the invention may be obtained by formation of $^{18}$F fluorodialkylamines and subsequent amide formation when the $^{18}$F fluorodialkylamine is reacted with a precursor containing, e.g. chlorine, P(O)Ph$_3$ or an activated ester.

A further approach for radiofluorination, which is particularly suitable for radiofluorination of peptides, is described in WO 03/080544 and uses thiol coupling. A CBP precursor compound of one of the following formulae:

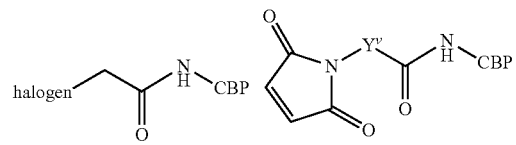

with a compound of Formula V:

$$^{18}F-X^V-SH \qquad (V)$$

wherein $Y^V$ is a linker of formula -(L)$_o$- wherein L is as previously defined, o is 1-10 and optionally includes 1-6 heteroatoms;

$X^V$ is a linker of formula -(L)$_p$- wherein L is as previously defined, p is 1-30 and optionally includes 1 to 10 heteroatoms; and, CBP is a collagen binding peptide as previously defined;

to give radiofluorinated imaging agents of formula (Va) or (Vb) respectively:

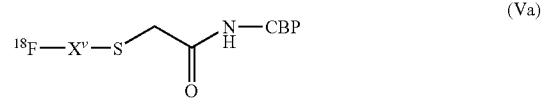

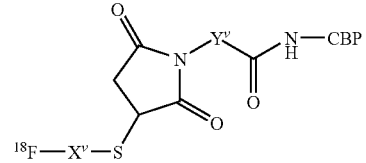

wherein $X^V$ and $Y^V$ are as defined above, and CBP is a collagen binding peptide as previously defined.

An additional approach particularly suitable for radiofluorination of peptides is described in WO 04/080492 and makes use of aminoxy coupling. Radiofluorination is carried out by reaction of a CBP precursor compound of formula (VI) with a compound of formula (VIa):

or,
by reaction of a CBP precursor compound of formula (VII) with a compound of formula (VIIa)

wherein;
R$^1$ is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;

$R^2$ is a functional group which, under mild conditions such as aqueous buffer, reacts site-specifically with $R^1$ yielding a stable conjugate. $R^2$ can be ammonia derivatives such as primary amine, secondary amine, hydroxylamine, hydrazine, hydrazide, aminoxy, phenylhydrazine, semicarbazide, or thiosemicarbazide, and is preferably a hydrazine, hydrazide or aminoxy group;

$R^3$ is a functional group which reacts site-specifically with $R^4$. $R^3$ can be ammonia derivatives such as primary amine, secondary amine, hydroxylamine, hydrazine, hydrazide, aminoxy, phenylhydrazine, semicarbazide, or thiosemicarbazide, and is preferably a hydrazine, hydrazide or aminoxy group;

$R^4$ is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;

to give a conjugate of formula (VIII) or (IX), respectively:

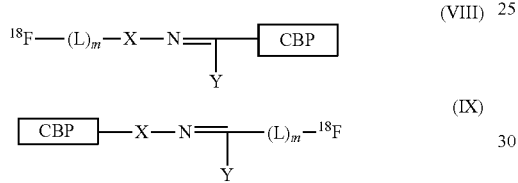

wherein X is —CO—NH—, —NH—, —O—, —NH-CONH—, or —NHCSNH—, and is preferably —CO—NH—, —NH— or —O—; Y is H, alkyl or aryl substituents, and wherein L is as previously defined and m 0-10.

Further details of synthetic routes to $^{18}$F-labelled derivatives are described by Bolton, J. Lab. Comp. Radiopharm., 45, 485-528 (2002).

Precursors are synthesized by first assembling the relevant CPB. Peptides may be assembled on a 0.1 mmol scale on MBHA-Rink amide resin (0.58 mmol/g), using an AB1433A synthesiser. Fmoc amino acid derivatives are activated in situ in a 10-fold molar excess using HBTU-HOBt-DIEA in NMP and Fmoc deprotected in 20% piperidine/NMP solution. After assembly the resin is transferred to a $N_2$ bubbler apparatus for coupling of a chemical group capable of reacting with an imaging moiety, as defined above. Kaiser tests are performed to ensure 100% conversion to the precursor compound. Cleavage from the solid support and removal of any side chain protecting groups is effected simultaneously. Excess TFA is thereafter removed in vacuo and precursor compounds precipitated by the addition of diethylether. Crude precursor compounds are liberated as a white solid following trituration with diethylether. The residue is dissolved in 0.1% TFA/MeCN:$H_2O$ (1:1), lyophilized, purified by HPLC and analysed by LC-MS.

The following are examples of preferred precursor compounds of the present invention (retaining numbering of corresponding imaging agents):

| # | Precursor |
|---|---|
| 1 | [Chelate II]-ANAALKAGELYKCILY-$NH_2$ (SEQ ID NO. 18) |
| 2 | [Chelate II]-PEG12-ANAALKAGELYKCILY-$NH_2$ (SEQ ID NO. 18) |
| 3 | [Chelate II]-DARKSEVQK-$NH_2$ (SEQ ID NO. 16) |
| 4 | [Chelate II]-GELYKCILY (SEQ ID NO. 5) |
| 5 | [Chelate II]-[PEG(12)]-GELYKCILY (SEQ ID NO. 5) |
| 6 | [Chelate II]-RRANAALKAGELYK-[Abu]-ILY (SEQ ID NO. 29) |
| 7 | [Chelate II]-CDARKSEVQKC (SEQ ID NO. 6) [cyclised via terminal Cys residues] |
| 8 | [Chelate II]-KELNLVYT (SEQ ID NO. 7) |
| 9 | [Chelate II]-CVWLWENC (SEQ ID NO. 11) [cyclised via terminal Cys residues] |
| 10 | [Chelate II]-CVWLWEQC-$NH_2$ (SEQ ID NO. 10) [cyclised via terminal Cys residues] |
| 11 | [Chelate II]-CVWTLPDQC (SEQ ID NO. 12) [cyclised via terminal Cys residues] |
| 12 | [Chelate II]-NGVFKYRPRYFLYKHAYFYPPLKRFPVQ (SEQ ID NO. 31) |
| 13 | [Chelate I]-ANAALKAGELYKCILY-$NH_2$ (SEQ ID NO. 18) |
| 14 | [Chelate I]-[PEG(12)]-ANAALKAGELYKCILY-$NH_2$ (SEQ ID NO. 18) |
| 15 | [Chelate I]-DARKSEVQK-$NH_2$ (SEQ ID NO. 16) |
| 16 | [Chelate I]-GELYKCILY (SEQ ID NO. 5) |
| 17 | [Chelate I]-[PEG(12)]-GELYKCILY (SEQ ID NO. 5) |
| 18 | [Chelate I]-RRANAALKAGELYK-[Abu]-ILY (SEQ ID NO. 29) |
| 19 | [Chelate I]-CDARKSEVQKC (SEQ ID NO. 6) [cyclised via terminal Cys residues] |
| 20 | [Chelate I]-KELNLVYT (SEQ ID NO. 7) |
| 21 | [Chelate I]-CVWLWENC (SEQ ID NO. 11) [cyclised via terminal Cys residues] |
| 22 | [Chelate I]-CVWLWEQC (SEQ ID NO. 10) [cyclised via terminal Cys residues] |
| 23 | [Chelate I]-CVWTLPDQC (SEQ ID NO. 12) [cyclised via terminal Cys residues] |
| 24 | [Chelate I]-NGVFKYRPRYFLYKHAYFYPPLKRFPVQ (SEQ ID NO. 31) |
| 38 | α-His-[Ac]-ANAALKAGELYK-[Abu]-ILY (SEQ ID NO. 19) |
| 39 | HYNIC-ANAALKAGELYK-[Abu]-ILY (SEQ ID NO. 19) |
| 40 | Chelate I-ANAALKAGELYK-[Abu]-ILY (SEQ ID NO. 19) |
| 41 | Chelate II-MIVVELTNPLKSSGIENGAFQGMKK (SEQ ID NO. 33) |
| 42 | Chelate I-ANAALKAGELYK-[Abu]-ILY-[PEG(4)]-[diglycoloyl]-$NH_2$ (SEQ ID NO. 19) |
| 43 | Chelate I-ANAALKAGELY-[NMe-Lys]-[Abu]-ILY-[PEG(4)]-[diglycoloyl]-$NH_2$ (SEQ ID NO. 24) |

In a third aspect, the present invention provides a pharmaceutical composition comprising the imaging agent as described above, together with a biocompatible carrier, in a form suitable for mammalian administration. In a preferred embodiment, the pharmaceutical composition is a radiopharmaceutical composition.

The "biocompatible carrier" is a fluid, especially a liquid, in which the imaging agent is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

Such pharmaceutical compositions are suitably supplied in either a container which is provided with a seal which is suitable for single or multiple puncturing with a hypodermic needle (e.g. a crimped-on septum seal closure) whilst maintaining sterile integrity. Such containers may contain single or multiple patient doses. Preferred multiple dose containers comprise a single bulk vial (e.g. of 10 to 30 cm³ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose", and are therefore preferably a disposable or other syringe suitable for clinical use. Where the pharmaceutical composition is a radiopharmaceutical composition, the pre-filled syringe may optionally be provided with a syringe shield to protect the operator from radioactive dose. Suitable such radiopharmaceutical syringe shields are known in the art and preferably comprise either lead or tungsten.

The pharmaceuticals of the present invention may be prepared from kits, as is described in the fourth aspect below. Alternatively, they may be prepared under aseptic manufacture conditions to give the desired sterile product. The pharmaceuticals may also be prepared under non-sterile conditions, followed by terminal sterilisation using e.g. gamma-irradiation, autoclaving, dry heat or chemical treatment (e.g. with ethylene oxide). Preferably, the pharmaceuticals of the present invention are prepared from kits.

As described above in relation to the first embodiment, for radiopharmaceutical compositions, the most preferred radioactive imaging moieties of the invention are $^{99m}$Tc, $^{123}$I, $^{11}$C and $^{18}$F.

In a fourth aspect, the present invention provides kits for the preparation of the pharmaceutical compositions of the third embodiment. Such kits comprise a suitable precursor of the second embodiment, preferably in sterile non-pyrogenic form, so that reaction with a sterile source of an imaging moiety gives the desired pharmaceutical with the minimum number of manipulations. Such considerations are particularly important in the case of radiopharmaceuticals, in particular for radiopharmaceuticals where the radioisotope has a relatively short half-life, for ease of handling and hence reduced radiation dose for the radiopharmacist. Hence, the reaction medium for reconstitution of such kits is preferably a "biocompatible carrier" as defined above, and is most preferably aqueous.

Suitable kit containers comprise a sealed container which permits maintenance of sterile integrity and/or radioactive safety, plus optionally an inert headspace gas (e.g. nitrogen or argon), whilst permitting addition and withdrawal of solutions by syringe. A preferred such container is a septum-sealed vial, wherein the gas-tight closure is crimped on with an overseal (typically of aluminium). Such containers have the additional advantage that the closure can withstand vacuum if desired e.g. to change the headspace gas or degas solutions.

Preferred aspects of the precursor when employed in the kit are as described for the second embodiment above. The precursors for use in the kit may be employed under aseptic manufacture conditions to give the desired sterile, non-pyrogenic material. The precursors may also be employed under non-sterile conditions, followed by terminal sterilisation using e.g. gamma-irradiation, autoclaving, dry heat or chemical treatment (e.g. with ethylene oxide). Preferably, the precursors are employed in sterile, non-pyrogenic form. Most preferably the sterile, non-pyrogenic precursors are employed in the sealed container as described above.

The precursor of the kit is preferably supplied covalently attached to a solid support matrix as described above in relation to the second embodiment.

For $^{99m}$Tc, the kit is preferably lyophilised and is designed to be reconstituted with sterile $^{99m}$Tc-pertechnetate (TcO$_4^-$) from a $^{99m}$Tc radioisotope generator to give a solution suitable for human administration without further manipulation. Suitable kits comprise a container (e.g. a septum-sealed vial) containing the uncomplexed chelating agent, together with a pharmaceutically acceptable reducing agent such as sodium dithionite, sodium bisulphite, ascorbic acid, formamidine sulphinic acid, stannous ion, Fe(II) or Cu(I); together with at least one salt of a weak organic acid with a biocompatible cation. By the term "biocompatible cation" is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium.

The kits for preparation of radiometal metal complex imaging agents may optionally further comprise a second, weak organic acid or salt thereof with a biocompatible cation, which functions as a transchelator. The transchelator is a compound which reacts rapidly to form a weak complex with the radiometal, then is displaced by the chelator of the kit. For technetium, this minimises the risk of formation of reduced hydrolysed technetium (RHT) due to rapid reduction of pertechnetate competing with technetium complexation. Suitable such transchelators are the weak organic acids and salts thereof described above, preferably tartrates, gluconates, glucoheptonates, benzoates, or phosphonates, preferably phosphonates, most especially diphosphonates. A preferred such transchelator is MDP, i.e. methylenediphosphonic acid, or a salt thereof with a biocompatible cation.

Also in relation to kits for the preparation of radiometal complexes, an alternative to use of the chelator in free form, the kit may optionally contain a non-radioactive metal complex of the chelator which, upon addition of the radiometal, undergoes transmetallation (i.e. ligand exchange) giving the desired product. Suitable such complexes for transmetallation are copper or zinc complexes.

The pharmaceutically acceptable reducing agent used in the $^{99m}$Tc imaging agent kit is preferably a stannous salt such as stannous chloride, stannous fluoride or stannous tartrate, and may be in either anhydrous or hydrated form. The stannous salt is preferably stannous chloride or stannous fluoride.

The kits may optionally further comprise additional components such as a radioprotectant, antimicrobial preservative, pH-adjusting agent or filler.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible cation. The "biocompatible cation" and preferred embodiments thereof are as described above.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the radiopharmaceutical composition post-reconstitution, i.e. in the radioactive diagnostic product itself. The antimicrobial preservative may, however, also optionally be used to inhibit the growth of potentially harmful micro-organisms in one or more components of the non-radioactive kit of the present invention prior to reconstitution. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human or mammalian administration. Suitable such pH-adjusting agents include pharmaceutically acceptable buffers, such as tricine, phosphate or TRIS [i.e. tris (hydroxymethyl)aminomethane], and pharmaceutically acceptable bases such as sodium carbonate, sodium bicarbonate or mixtures thereof. When the precursor is employed in acid salt form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The imaging agents of the invention are useful for in vivo imaging. Accordingly, in a fifth aspect, the present invention provides an imaging agent of the invention for use in an in vivo diagnostic or imaging method, e.g. SPECT or PET. Preferably said method relates to the in vivo imaging of a condition in which collagen formation is upregulated and therefore has utility in the diagnosis of conditions associated with fibrosis, such as idiopathic pulmonary fibrosis, asthma, chronic obstructive pulmonary disease, scleroderma, diabetic retinopathy, AMD, atherosclerosis, vulnerable plaque, diabetic nephropathy, glomerulosclerosis, IgA nephropathy, liver fibrosis, rheumatoid arthritis and congestive heart failure. Most preferably, said method of in vivo diagnostic or imaging method is a method useful in the diagnosis of chronic obstructive pulmonary disease, diabetic retinopathy, AMD, atherosclerosis, vulnerable plaque, diabetic nephropathy, glomerulosclerosis, liver fibrosis and congestive heart failure, especially preferably liver fibrosis.

This aspect of the invention also provides a method for the in vivo diagnosis or imaging in a subject of a condition in which collagen formation is upregulated, comprising prior administration of the pharmaceutical composition of the third aspect of the invention. Said subject is preferably a mammal and most preferably a human. In an alternative embodiment, this aspect of the invention furthermore provides for the use of the imaging agent of the invention for imaging in vivo of a condition in which collagen formation is upregulated in a subject wherein said subject is previously administered with the pharmaceutical composition of the third aspect of the invention.

By "previously administered" is meant that the step involving the clinician, wherein the pharmaceutical is given to the patient e.g., intravenous injection, has already been carried out. This aspect of the invention also encompasses use of the imaging agent of the first embodiment for the manufacture of pharmaceutical for the diagnostic imaging in vivo of a condition in which collagen formation is upregulated.

In a sixth aspect the invention provides a method of monitoring the effect of treatment of a human or animal body with a drug to combat a condition in which collagen formation is upregulated, said method comprising administering to said body an imaging agent of the invention and detecting the uptake of said imaging agent, said administration and detection optionally but preferably being effected repeatedly, e.g. before, during and after treatment with said drug.

BRIEF DESCRIPTION OF THE EXAMPLES

Example 1 describes the synthesis of Chelate I.
Example 2 describes the synthesis of the glutarylamide derivative of Chelate I.
Example 3 describes the synthesis of Chelate II.
Examples 4 to 17 describe the synthesis of Imaging Agents 1, 3, 8, 10, 29, and 35 to 43.
Example 18 describes a method for evaluating the in vitro collagen-binding affinity of imaging agents of the invention.
Example 19 describes the in vivo biodistribution of Imaging Agent 1 of the invention in an animal model of liver fibrosis.
Example 20 describes an in vivo model suitable for evaluation of potential of compounds for imaging liver fibrosis (bile duct ligation model).

EXAMPLES

List of Abbreviations Used in Examples

| Acm | acetamidomethyl |
| --- | --- |
| ACN | acetonitrile |
| AcOH | acetic acid |
| BDL | bile duct ligation |
| Boc | t-butoxycarbonyl |
| DCM | dichloromethane |
| DIEA | diisopropylethylamine |
| DMF | dimethyl formamide |
| ESI-MS | electrospray ionisation mass spectrometry |
| HBTU | O-Benzotriazole-N,N,N',N'-tetramethyl-uronium-hexafluoro-phosphate |
| HOBt | N-Hydroxybenzotriazole |
| HPLC | high performance liquid chromatography |
| IR | infra red |
| LC-MS | liquid chromatography-mass spectrometry |
| MS | mass spectrometry |
| NMM | N-Methylmorpholine |
| NMP | N-Methylpyrrolidone |
| NMR | nuclear magnetic resonance |
| OtBu | β-t-butyl ester |
| PyAOP | (7-azabenzotriazole-1-yloxy) tripyrrolidinophosphonium hexafluorophosphate |
| RF | retention fraction |
| s.c | subcutaneous |
| TFA | trifluoroacetic acid |
| THF | tetrahydrofuran |
| TLC | thin layer chromatography |
| Trt | Tripheylmethyl |

Example 1

Synthesis of Chelate I [bis[N-(1,1-dimethyl-2-N-hydroxyimine propyl)-2-aminoethyl]-(2-aminoethyl) methane]

(Step a): Preparation of tris(methyloxycarbonylmethyl)methane 3-(methoxycarbonylmethylene)glutaric acid dimethyl-ester (89 g, 267 mmol) in methanol (200 ml) was shaken with (10% palladium on charcoal: 50% water) (9 g) under an atmosphere of hydrogen gas (3.5 bar) for (30 h). The solution was filtered through kieselguhr and concentrated in vacuo to give 3-(methoxycarbonylmethyl)glutaric acid dimethylester as an oil, yield (84.9 g, 94%).

NMR $^1$H(CDCl$_3$), δ 2.48 (6H, d, J=8 Hz, 3×CH$_2$), 2.78 (1H, hextet, J=8 Hz CH,) 3.7 (9H, s, 3×CH$_3$).

NMR $^{13}$C(CDCl$_3$), δ 28.6, CH; 37.50, 3×CH$_3$; 51.6, 3×CH$_2$; 172.28, 3×COO.

(Step b): Amidation of trimethylester with p-methoxy-benzylamine

Tris(methyloxycarbonylmethyl)methane [2 g, 8.4 mmol] was dissolved in p-methoxy-benzylamine (25 g, 178.6 mmol). The apparatus was set up for distillation and heated to 120° C. for 24 hrs under nitrogen flow. The progress of the reaction was monitored by the amount of methanol collected. The reaction mixture was cooled to ambient temperature and 30 ml of ethyl acetate was added, then the precipitated triamide product stirred for 30 min. The triamide was isolated by filtration and the filter cake washed several times with sufficient amounts of ethyl acetate to remove excess p-methoxybenzylamine. After drying 4.6 g, 100%, of a white powder was obtained. The highly insoluble product was used directly in the next step without further purification or characterisation.

(Step c): Preparation of 1,1,1-tris[2-(p-methoxybenzylamino)ethyl]methane

To a 1000 ml 3-necked round bottomed flask cooled in a ice-water bath the triamide from step 2(a) (10 g, 17.89 mmol) is carefully added to 250 ml of 1M borane solution (3.5 g, 244.3 mmol) borane. After complete addition the ice-water bath is removed and the reaction mixture slowly heated to 60° C. The reaction mixture is stirred at 60° C. for 20 hrs. A sample of the reaction mixture (1 ml) was withdrawn, and mixed with 0.5 ml 5N HCl and left standing for 30 min. To the sample 0.5 ml of 50 NaOH was added, followed by 2 ml of water and the solution was stirred until all of the white precipitate dissolved. The solution was extracted with ether (5 ml) and evaporated. The residue was dissolved in acetonitrile at a concentration of 1 mg/ml and analysed by MS. If mono- and diamide (M+H/z=520 and 534) are seen in the MS spectrum, the reaction is not complete. To complete the reaction, a further 100 ml of 1M borane THF solution is added and the reaction mixture stirred for 6 more hrs at 60° C. and a new sample withdrawn following the previous sampling procedure. Further addition of the 1M borane in THF solution is continued as necessary until there is complete conversion to the triamine.

The reaction mixture is cooled to ambient temperature and 5N HCl is slowly added, [CARE: vigorous foam formation occurs!]. HCl was added until no more gas evolution is observed. The mixture was stirred for 30 min and then evaporated. The cake was suspended in aqueous NaOH solution (20-40%; 1:2 w/v) and stirred for 30 minutes. The mixture was then diluted with water (3 volumes). The mixture was then extracted with diethylether (2×150 ml) [CARE: do not use halogenated solvents]. The combined organic phases were then washed with water (1×200 ml), brine (150 ml) and dried over magnesium sulphate. Yield after evaporation: 7.6 g, 84% as oil.

NMR $^1$H(CDCl$_3$), δ: 1.45, (6H, m, 3×CH$_2$; 1.54, (1H, septet, CH); 2.60 (6H, t, 3×CH$_2$N); 3.68 (6H, s, ArCH$_2$); 3.78 (9H, s, 3×CH$_3$O); 6.94 (6H, d, 6×Ar). 7.20 (6H, d, 6×Ar).

NMR $^{13}$C(CDCl$_3$), δ: 32.17, CH; 34.44, CH$_2$; 47.00, CH$_2$; 53.56, ArCH$_2$; 55.25, CH$_3$O; 113.78, Ar; 129.29, Ar; 132.61; Ar; 158.60, Ar.

(Step d): Preparation of 1,1,1-tris(2-aminoethyl)methane 1,1,1-tris[2-(p-methoxybenzylamino)ethyl]methane (20.0 gram, 0.036 mol) was dissolved in methanol (100 ml) and Pd(OH)$_2$ (5.0 gram) was added. The mixture was hydrogenated (3 bar, 100° C., in an autoclave) and stirred for 5 hours. Pd(OH)$_2$ was added in two more portions (2×5 gram) after 10 and 15 hours respectively. The reaction mixture was filtered and the filtrate was washed with methanol. The combined organic phase was evaporated and the residue was distilled under vacuum (1×10$^{-2}$, 110° C.) to give 2.60 gram (50%) of 1,1,1-tris(2-aminoethyl)methane.

NMR $^1$H(CDCl$_3$), δ 2.72 (6H, t, 3×CH$_2$N), 1.41 (H, septet, CH), 1.39 (6H, q, 3×CH$_2$).

NMR $^{13}$C(CDCl$_3$), δ 39.8 (CH$_2$NH$_2$), 38.2 (CH$_2$.), 31.0 (CH).

(Step e): Preparation of Chelate I

To a solution of tris(2-aminoethyl)methane (4.047 g, 27.9 mmol) in dry ethanol (30 ml) was added potassium carbonate anhydrous (7.7 g, 55.8 mmol, 2 eq) at room temperature with vigorous stirring under a nitrogen atmosphere. A solution of 3-chloro-3-methyl-2-nitrosobutane (7.56 g, 55.8 mol, 2 eq) was dissolved in dry ethanol (100 ml) and 75 ml of this solution was dripped slowly into the reaction mixture. The reaction was followed by TLC on silica [plates run in dichloromethane, methanol, concentrated (0.88 sg) ammonia; 100/30/5 and the TLC plate developed by spraying with ninhydrin and heating]. The mono-, di- and tri-alkylated products were seen with RF's increasing in that order. Analytical HPLC was run using RPR reverse phase column in a gradient of 7.5-75% acetonitrile in 3% aqueous ammonia. The reaction was concentrated in vacuo to remove the ethanol and resuspended in water (110 ml). The aqueous slurry was extracted with ether (100 ml) to remove some of the trialkylated compound and lipophilic impurities leaving the mono and desired dialkylated product in the water layer. The aqueous solution was buffered with ammonium acetate (2 eq, 4.3 g, 55.8 mmol) to ensure good chromatography. The aqueous solution was stored at 4° C. overnight before purifying by automated preparative HPLC.

Yield (2.2 g, 6.4 mmol, 23%).

Mass spec; Positive ion 10 V cone voltage. Found: 344; calculated M+H=344.

NMR $^1$H(CDCl$_3$), δ1.24 (6H, s, 2×CH$_3$), 1.3 (6H, s, 2×CH$_3$), 1.25-1.75 (7H, m, 3×CH$_2$, CH), (3H, s, 2×CH$_2$), 2.58 (4H, m, CH$_2$N), 2.88 (2H, t CH$_2$N$_2$), 5.0 (6H, s, NH$_2$, 2×NH, 2×OH).

NMR $^1$H ((CD$_3$)$_2$SO) δ1.1 4×CH; 1.29, 3×CH$_2$; 2.1 (4H, t, 2×CH$_2$);

NMR $^{13}$C((CD$_3$)$_2$SO), δ9.0 (4×CH$_3$), 25.8 (2×CH$_3$), 31.0 2×CH$_2$, 34.6 CH$_2$, 56.8 2×CH$_2$N; 160.3, C=N.

HPLC conditions: flow rate 8 ml/min using a 25 mm PRP column

A=3% ammonia solution (sp.gr=0.88)/water; B=Acetonitrile

| Time | % B |
|------|-----|
| 0    | 7.5 |
| 15   | 75.0 |
| 20   | 75.0 |
| 22   | 7.5 |
| 30   | 7.5 |

Load 3 ml of aqueous solution per run, and collect in a time window of 12.5-13.5 min.

Example 2

Synthesis of the qlutarylamide derivative of Chelate I [bis[(1,1-dimethyl-2-N-hydroxyimine propyl)2-aminoethyl]-(2-(Glutarylamide)ethyl)methane]

Chelate I (0.5 g, 1.45 mmol) in dry acetonitrile (50 ml) and triethylamine (150 mg, 1.45 mmol) under an atmosphere of nitrogen was cooled on an ice bath to 0° C. Glutaric anhydride (165 mg, 1.45 mmol) was added to the stirred reaction and allowed to warm to room temperature and left to stir overnight. The precipitate that formed overnight was collected by filtration and dried in vacuo to give an impure sample of the title compound (267 mg, 0.583 mmol, 40%). The filtrate was concentrated in vacuo to give a colourless glass which together with the precipitate that had been collected was redissolved in 5% 0.880 sg ammonia, water (50 ml) and purified by automated preparative HPLC.

HPLC conditions: flow rate 8 ml/min, using a 150 mm×25 mm PRP column

Sample loaded in 2 ml of solution per run.

A=3% ammonia solution (sp.gr=0.88)/water.

B=Acetonitrile

| Time | % B |
|------|-----|
| 0    | 7.5 |
| 15   | 75.0 |
| 20   | 75.0 |
| 22   | 7.5 |
| 31   | 7.5 |

The required product eluted at 15.25-16.5 min. The product solution was evaporated in vacuo to give (304 mg, 0.68 mmol, 47%) of a colourless glassy foam m.p. 54.8° C. The product analysed as one spot on both TLC and analytical HPLC.

NMR $^1$H(DMSO), 0.7 (12H, s, 4×CH$_3$), 0.85 (4H, m, 2×CH$_2$), 1.0 (1H, m, CH), 1.3 (6H, s, 2×CH$_3$), 1.3 (4H, m, 2×CH$_2$), 1.6 (2H, m, CH$_2$), 1.75 (6, m, 3×CH$_2$), 2.6 (2, m, 2×OH) 3.2 (2H, t, NH) 7.3 (1H, t, NH).

NMR $^{13}$C(CD$_3$SO) 8.97, 20.51, 20.91, 25.09, 25.60, 31.06, 33.41, 33.86, 56.89, 66.99 160.07, 1712.34, 174.35 174.56

M/S C$_{22}$H$_{43}$N$_5$O$_5$ M+H=457 Found 457.6

Example 3

Synthesis of (8-Amino-2-{[tert-butoxycarbonyl-(2-tert-carbonylamino-ethyl)-amino]-methyl}-octyl)-(2-tert-butyloxycarbonylamino-ethyl)-carbamic acid tert-butyl ester (Boc-protected Chelate II)

Step (a): 2-(6-Chloro-hexyloxy)tetrahydropyran

6-Chlorohexanol (6.85 g, 10 mmol) and p-toluenesulphonic acid (500 mg), were dissolved in dry ether (75 ml) and cooled to 0-5° C. in an ice bath. Dihydropyran (4.3 g, 10 mmol) in dry ether (25 ml) was added dropwise with constant stirring over a 30 minute period. After complete addition, the cooling bath was removed and stirring continued for 16 hours. The solution was extracted with water (50 ml×2), dried (MgSO$_4$), filtered and the solvent evaporated under reduced pressure to leave a pale yellow oil. This oil was shown by $^{13}$C NMR spectroscopy to be sufficiently pure to be used without purification in the subsequent reactions. Yield 10.1 g (91%).

$^{13}$C NMR (CDCl$_3$): δ 19.7 (CH$_2$), 25.5 (CH$_2$), 25.6 (CH$_2$), 26.7 (CH$_2$), 29.6 (CH$_2$), 30.8 (CH$_2$), 32.6 (CH$_2$), 45.0 (CH$_2$Cl), 62.3 (OCH$_2$), 67.4 (OCH$_2$), 98.8 (OCHO).

$^1$H NMR (CDCl$_3$): δ 1.30-1.71 (14H, m, CH$_2$×7), 3.24-3.32 (1H 3.41-3.48 (3H, m CH and CH$_2$), 3.60-3.67 (1H, m, CH), 3.72-3.82 (1H, bm, CH), 4.44-4.49 (1H, bm, OCHO).

Step (b): 2-[6-(Tetrahyhydro-pyran-2-yloxy)-hexyl]-malonic acid diethyl ester

Sodium (1.13 g, 49 mmol) in small quantities was dissolved in dry ethanol (100 ml) with constant stirring under a blanket of dry nitrogen. Diethyl malonate (8.0 g, 50 mmol) was added in one portion and the solution heated at 60° C. for 1 hour. 2-(6-Chloro-hexyloxy)-tetrahydropyran (9.3 g, 42.2 mmol) was added in one portion and the temperature raised to 75-80° C. and maintained at this level for 24 hours. After cooling, the inorganic solid was removed by filtration and solvent evaporated from the filtrate. The residue was dissolved in CH$_2$Cl$_2$ (50 ml), extracted with water (30 ml×2), dried (MgSO$_4$) filtered and volatiles removed to leave a pale yellow oil. This oil was subject to chromatography on silica gel using pet ether 40:60/ether (200:40) as the eluent. The required product eluted with an r$_f$=0.15 and was isolated as a colourless oil. Yield 8.7 g, (60%).

$^{13}$C NMR (CDCl$_3$): δ 14.0 (CH$_3$×2), 19.6 (CH$_2$), 25.5 (CH$_2$), 27.2 (CH$_2$), 28.6 (CH$_2$), 29.0 (CH$_2$), 29.6 ((CH$_2$), 30.0 (CH$_2$), 30.8 (CH$_2$), 52.0 (CH), 61.2 (OCH$_2$×2), 62.2 (OCH$_2$), 67.4 (OCH$_2$), 98.8 (OCHO), 169.4 (C=O×2).

$^1$H NMR (CDCl$_3$): δ 1.10-1.25 (14H, m, CH$_3$×2, CH$_2$×4), 1.36-1.50 (6H, bm, CH$_2$×3), 1.70-1.81 (2H, bm, CH$_2$), 3.17-3.28 (2H, m, CH$_2$), 3.56-3.66 (1H, m, CH), 3.70-3.80 (1H, m, OCH), 4.04-4.16 (4H, m, OCH$_2$×2), 4.03-4.08 (1H, m, OCHO).

Step (c): N,N'-Bis-(2-amino-ethyl)-2-[6-(tetrahydro-pyran-2-yloxy)-hexyl]-malonamide 2-[6-(Tetrahyhydro-pyran-2-yloxy)-hexyl]-malonic acid diethyl ester (5.1 g, 14.8 mmol) was dissolved in 1,2-diaminoethane (10 g, 167 mmol) and stirred at room temperature for 16 hours. Volatiles were removed in vacuo (40-50° C. at 0.01 mm Hg) to leave a pale green viscous residue which was subjected to column chromatography eluting with CH$_2$Cl$_2$/MeOH/NH$_4$OH (50:50:5). The title compound eluted with an r$_f$0.2 and was collected as a pale green viscous oil which solidifies on standing. (Yield 3.9 g, 71%).

$^{13}$C NMR (CDCl$_3$): δ 19.8 (CH$_2$), 25.5 (CH$_2$), 26.0 (CH$_2$), 27.5 (CH$_2$), 29.2 (CH$_2$), 29.7 (CH$_2$), 30.8 (CH$_2$), 31.9 (CH$_2$), 41.0 (NCH$_2$×2), 41.9 (NCH$_2$×2), 54.6 (CH), 62.5 (OCH$_2$), 67.5 (OCH$_2$), 98.9 (OCHO), 171.6 (C=O×2).

$^1$H NMR (CDCl$_3$): δ 1.15-1.28 (6H, bs, CH$_2$×3), 1.39-1.44 (6H, bm, CH$_2$×3), 1.69-1.74 (4H, bm, CH$_2$×2), 2.64 (4H, bs, NH$_2$×2), 2.73 4H, t, J=6 Hz, CH$_2$×2), 3.08-3.29 (6H, m, CH$_2$×3), 3.35-3.41 (1H, m CH), 3.55-3.63 (1H, m, CH), 3.70-3.78 (1H, m, CH), 4.43 (1H, bt, J=4 Hz, OCHO), 7.78 (2H, bt, J=5 Hz, OCNH×2)

IR (thin film) cm$^{-1}$:—3417, 3082, 2936, 2862, 1663, 1558, 1439, 1354, 1323, 1261, 1200, 1189, 1076, 1026, 956, 907, 867, 810.

Step (d): N,N'-Bis(2-aminoethyl)-2-(6-hydroxy-hexyl)-malonamide

N,N'-Bis(2-aminoethyl)-2-[6-(tetrahydro-pyran-2-yloxy)-hexyl]-malonamide (3.9 g, 10.6 mmol), p-toluenesulphonic acid monohydrate (8.5 g, 3 mmol) and ethanol (50 ml) were heated under reflux at 70-75° C. for 16 hours. After cooling, concentrated ammonium hydroxide (0.880) was added dropwise until a permanent pH of 9 was achieved. The precipitated white solid was removed by filtration through Celite and the filter cake washed with ethanol (30 ml). The ethanol was removed under reduced pressure (15 mm Hg, 40° C.) to leave a semi-solid wax. This residue was subjected to chromatography on silica-gel eluting with CH$_2$Cl$_2$/MeOH/NH$_4$OH (100:50:10) and the title compound found to have an r$_f$=0.2. This product was collected and co-evaporated with ethanol (100 ml×3) to remove any residual water. A pale green viscous residue was obtained which solidifies on standing. (Yield 2.1 g, 69%).

$^{13}$C NMR (CD$_3$OD): δ 25.4 (CH$_2$), 27.3 (CH$_2$), 28.9 (CH$_2$), 30.4 (CH$_2$), 32.2 (CH$_2$), 40.6 (NCH$_2$×2), 41.7 (NCH$_2$×2), 54.1 (CH), 61.6 (CH$_2$OH), 171.7 (C=O×2).

$^1$H NMR (CD$_3$OD): δ 1.28-1.38 (6H, bs, CH$_2$×3), 1.46-1.55 (2H, bm, CH$_2$), 1.79-1.87 (2H, bm, CH$_2$), 2.73 (4H, t, J=6 Hz, H$_2$NCH$_2$×2), 3.13 (1H t, J=7 Hz, CH), 3.27 (4H, dt, J=6 and 2 Hz, HNCH$_2$×2), 3.53 (2H t, J=7 Hz OCH$_2$).

IR (thin film) cm$^{-1}$:—3364, 2932, 2862, 2527, 1663, 1558, 1462, 1327, 1223, 1192, 1034.

Mass spec (Fabs) m/e:—Calculated for C$_{13}$H$_{29}$N$_4$O$_3$ (M+H) 289 Found 289.

Step (e): (2-tert-Butoxycarbonylamino-ethyl-2-{[tert-butoxycarbonyl-(2-tert-butoxycarbonylamino-ethyl)-amino-ethyl)-amino]methyl}-hydroxy-octyl)-carbonic acid tert-butyl ester Under a blanket of dry nitrogen, neat borane-dimethylsulphide adduct (15 ml, 150 mmol) was added dropwise via a syringe to a stirred mixture of N,N'-bis-(2-aminoethyl)-2-(6-hydroxyhexyl)malonamide (2.1 g, 7.3 mmol) in dioxane (50 ml). After complete addition, the mixture was heated gently under reflux at 110° C. for 5 days. During this period some white solid remained. After cooling the volatiles were removed under reduced pressure to leave a white solid to which methanol (50 ml) was added dropwise giving a colourless solution. This solution was heated under reflux for 3 hours, cooled, conc. HCl (5 ml) added and heating continued under reflux at 70-75° C. for 48 hours. The solvent was removed to leave a viscous green residue which was co-evaporated with methanol (100 ml×3) to leave a pale green solid. This solid was redissolved in dry methanol and anhydrous potassium carbonate (4.0 g, 30 mmol) added followed by di-tert-butyl dicarbonate (7.0 g, 32 mmol). The mixture was stirred at room temperature for 48 hours. The inorganic solid was removed by filtration through Celite and solvent evaporated from the filtrate to leave a viscous residue. This residue was mixed with water (50 ml) and extracted with CH$_2$Cl$_2$ (50 ml×3). The organic fractions were combined, dried (MgSO$_4$), filtered and the solvent evaporated to leave a pale yellow residue.

Note: At this point it is convenient to monitor the reaction by $^{13}$C NMR.

The residue was subjected to chromatography on silica gel using CH$_2$Cl$_2$/MeOH (95:5) as eluent. The title compound eluted with an r$_f$=0.41 and was isolated as a colourless viscous oil (Yield 2.5 g, 52%).

$^{13}$C NMR (CDCl$_3$): δ 25.6 (CH$_2$), 26.4 (CH$_2$), 28.4 (CH$_3$× 12), 29.8 (CH$_2$×2), 32.6 (CH$_2$), 36.5 (very broad, CH), 39.2 (NCH$_2$×2, adjacent CH), 46.9 (broad singlet, HNCH$_2$×2), 50.0 (broad singlet, NCH$_2$×2), 62.4 (HOCH$_2$), 79.0 (OC×2), 79.9 (OC×2), 156.4 (broad singlet C=O×4)

$^1$H NMR (CDCl$_3$): δ 1.05-1.18 (8H, bs, CH$_2$×4), 1.27 (18H, s, CH$_3$×6, t-butyl), 1.31 (18H, s, CH$_3$×6, t-butyl), 1.41 (2H, m, CH$_2$), 1.81 (1H bs, CH), 2.63 (1H, bs, OH), 2.98 (4H, bs, NCH$_2$×2), 3.11 (8H, bs, NCH$_2$×4), 3.44 (2H, t, J=8 Hz, CH$_2$O), 5.2 (2H, bs, NH×2)

IR (thin film) cm$^{-1}$:—3350, 2976, 2931, 2859, 1674, 1516, 1455, 1418, 1393, 1260, 1250, 1165, 1069, 965, 871, 775.

Mass Spec (Fabs) m/e:—Calculated for C$_{33}$H$_{65}$N$_4$O$_9$ (M+H) 661. Found 661.

Step (f): Toluene-4-sulfonic acid 8-[tert-butoxycarbonyl-(2-tert-butoxycarbonylamino-ethyl-amino]-7-{[tert-butoxycarbonyl-(2-tert-butoxycarbonylamino-ethyl)-amino]-methyl}-octyl Ester (2-tert-Butoxycarbonylamino-ethyl-2-{[tert-butoxycarbonyl-(2-tert-butoxycarbonylaminoethylamino]-methyl}-8-hydroxyoctyl)-carbonic acid tert-butyl ester (2.52 g, 3.82 mmol), p-toluenesulfonyl chloride (1.0 g, 5.2 mmol), triethylamine (1.3 g, 12.8 mmol) and CH$_2$Cl$_2$ (30 ml) were stirred at room temperature with the slow evaporation of solvent. The reaction was monitored by carbon NMR and after 3 days little starting material remained. The reaction volume was made up to 30 ml with CH$_2$Cl$_2$, extracted with water (50 ml×3), dried (MgSO$_4$), filtered and the solvent evaporated to leave a brown residue. This residue was subjected to chromatography on silica gel using CH$_2$Cl$_2$/MeOH (100:5) as eluent. The first compound to elute was unreacted tosyl chloride with an r$_f$=0.95. The title compound eluted with an r$_f$=0.2 and was isolated as a pale yellow viscous oil. Yield (1.20 g, 39%).

$^{13}$C NMR (CDCl$_3$): δ 21.7 (CH$_3$ tosyl), 25.3 (CH$_2$), 26.3 (CH$_2$), 28.5 (CH$_3$×12), 28.8 (CH$_2$), 29.5 (CH$_2$), 29.9 (CH$_2$), 36.5 (CH very broad), 39.4 (NCH$_2$×2), 47.0 (broad NCH$_2$×2), 50.5 (broad, NCH$_2$×2), 70.6 (TsOCH$_2$), 79.1 (OC×2), 80.0 (OC×2), 127.9 (CH×2), 129.9 (CH×2), 133.2 (C), 144.7 (C—S Ts), 156.1 (broad, C=O×4).

$^1$H NMR (CDCl$_3$): δ 1.16 (8H, bs, CH$_2$×4), 1.35 (18H, s, CH$_3$×6), 1.39 (18H, s, CH$_3$×6), 1.88 (1H, bs, CH), 2.38 (3H, s, CH$_3$ Tosyl), 3.10-3.12 (4H, bs, NCH$_2$×2), 3.19 (8H, bs, NCH$_2$×4), 3.93 (2H, t, J=7 Hz, CH$_2$OTs), 5.0 (1H, bs, NH), 5.08 (1H, bs, NH), 7.29 (2H, d, J=8 Hz, CH×2, Ar), 7.72 (2H, d, J=8 Hz CH×2, Ar)

IR (thin film) cm$^{-1}$: —3360, 2974, 2932, 2862, 1693, 1516, 1479, 1418, 1391, 1366, 1250, 1177, 1069, 959, 816, 775.

Mass Spec (Fabs) m/e:—Calculated for C$_{40_1-171}$N$_4$O$_{11}$S (M+H) 815 Found 815

Step (q): (8-Azido-2-{[tert-butoxycarbonyl-(2-tert-carbonylamino-ethyl)-amino]-methyl}-octyl)-(2-tert-butyloxycarbonylamino-ethyl)-carbamic acid tert-butyl ester Toluene-4-sulfonic acid 8-[tert-butoxycarbonyl-(2-tert-butoxycarbonylaminoethyl-amino]-7-{[tert-butoxycarbonyl-(2-tert-butoxycarbonylaminoethylamino]methyl}-octyl ester (1.105 g, 1.36 mmol), sodium azide (350 mg, 5.4 mmol) and methanol (10 ml) were heated under reflux at 70-75° C. for 16 hours. After cooling, methanol was removed at room temperature under reduced pressure until about 1-2 ml remained. This residue was diluted with water (25 ml) and extracted with $CH_2Cl_2$ (25 ml×4). The organic extracts were combined, dried ($MgSO_4$), filtered and volatiles evaporated at room temperature (Note: Azides are potentially explosive and this step should be carried out behind a safety shield) to leave a pale yellow viscous residue which was the desired compound in a pure state. (Yield 820 mg, 88%).

$^{13}$C NMR ($CDCl_3$): δ 26.3 ($CH_2$), 26.5 ($CH_2$), 28.3 ($CH_3$×12), 28.7 ($CH_2$), 29.6 ($CH_2$), 29.8 ($CH_2$), 36.8 (broad, CH), 39.3 ($NCH_2$×2), 46.9 (Broad, $NCH_2$×2), 50.0 (broad, $NCH_2$×2), 51.3 ($CH_2N_3$), 79.0 (OC×2), 79.8 (OC×2), 156.0 (C=O×4).

$^1$H NMR ($CDCl_3$): δ1.16 (8H, bs, $CH_2$×4), 1.29 (18H, s $CH_3$×6), 1.33 (18H, s, $CH_3$×6), 1.47 (2H, bt, J=6.5 Hz $CH_2$ adjacent CH), 1.86 (1H, bs, CH), 2.95-3.05 (4H, bs, $NCH_2$×2), 3.05-3.20 (10H, bs, $NCH_2$×4 and $CH_2N_3$), 5.09 (2H, bs, NH×2)

IR (thin film) cm$^{-1}$:—3350, 2974, 2932, 2860, 2097 (Strong band $N_3$), 1694, 1520, 1470, 1418, 1391, 1366, 1250, 1167, 1069, 870, 777.

Step (h): (8-Amino-2-{[tert-butoxycarbonyl-(2-tert-carbonylamino-ethyl)-amino]-methyl}-octyl)-(2-tert-butyloxycarbonylamino-ethyl)-carbamic acid tert-butyl ester (Chelate II)

(8-Azido-2-{[tert-butoxycarbonyl-(2-tert-carbonylamino-ethyl)-amino]-methyl}-octyl)-(2-tert-butyloxycarbonylamino-ethyl)-carbamic acid tert-butyl ester (820 mg, 1.20 mmol), 10% palladium on charcoal (100 mg) and methanol (10 ml) were treated with hydrogen gas under a pressure of 30 atmospheres at room temperature for 16 hours. The solids were removed by filtration through Celite and the filter cake was washed with methanol (50 ml). Volatiles were removed from the filtrate to leave a viscous oil which was the desired material in a pure state. (Yield 700 mg, 89%).

$^{13}$C NMR ($CDCl_3$): δ 26.4 ($CH_2$), 26.6 ($CH_2$), 28.4 ($CH_3$×12), 32.9 ($CH_2$×2), 36.8 (broad, CH). 39.2 ($NCH_2$×2), 41.8 ($H_2NCH_2$), 46.9 (broad, $NCH_2$×2), 49.8 (broad, $NCH_2$×2), 78.9 (OC×2), 79.7 (OC×2), 156.0 (C=O×4).

$^1$H NMR ($CDCl_3$): δ1.08 (8H, bs, $CH_2$×4), 1.23 (18H, s, $CH_3$×6), 1.27 (20H, bs, $CH_3$×6 and $CH_2$), 1.77 (1H, bs, CH), 2.40 (2H, bs, $NH_2$), 2.50 (2H, t, J=7 Hz, $CH_2NH_2$), 2.97 (4H, bm, $NCH_2$×2), 3.00-3.16 (8H, bm, $NCH_2$×4), 5.21 (1H, bs, NH), 5.30 (1H, bs, NH).

IR (thin film) cm$^{-1}$:—3360, 1693, 1520, 1459, 1418, 1392, 1367, 1250, 1170, 1068, 964, 922, 871, 775, 733.

Mass Spec (Fabs) m/e:—Calculated for $C_{33}H_{66}N_5O_8$ (M+H) 660 Found 660.

Example 4

Synthesis of Imaging Agent 1

(a) Synthesis of Precursor 1

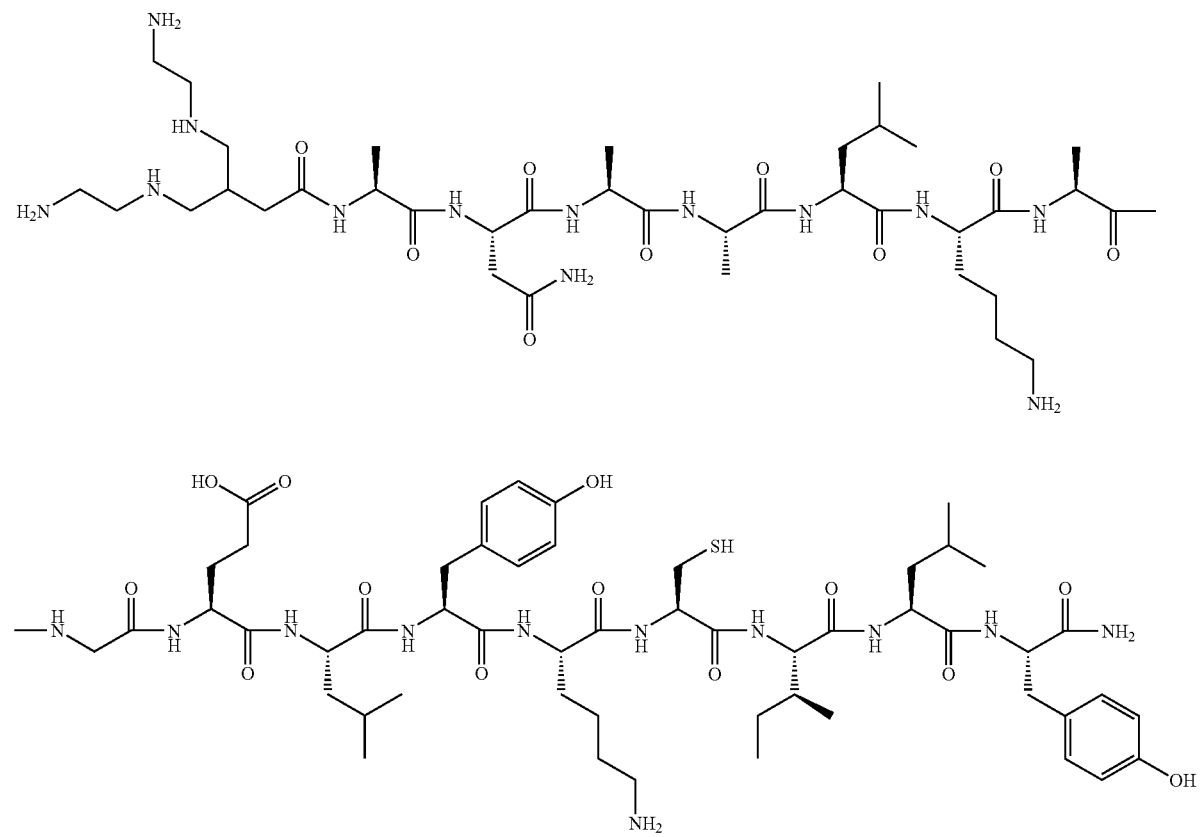

The peptide was assembled on an ABI 433A automated synthesiser by using Nova Biochem Rink MBHA resin (0.58 mmole/g or 0.72 mmole/g). The peptide was synthesised on a 0.1 mmole scale or a 0.25 mmole scale. Standard protocol was used.

Coupling reagent HBTU/HOBt, Base: DIEA, Solvent: NMP.

HPLC mobile phases A) 0.1% TFA/$H_2O$ B) 0.1% TFA/MeCN.

HPLC Columns: Analytical: Phenomenex, Gemini, 250× 4.6 mm, 5 μm

Prep: Phenomenex, Gemini, 250×21 mm, 10 μm.

Subsequent to the automatic assembly the peptide resin (130 mg, 0.05 mmole) was swollen for 10 min in DMF. TetraBoc-Chelate II NHS ester (148 mg, 0.2 mmole; Boc-protected Chelate II described in Example 3) was mixed with PyAOP (104 mg, 0.2 mmole) and NMM (40 μl, 0.4 mmole) in DMF (5 ml) for 3 min. NMM (20 μl, 0.2 mmol) was added to the resin and thereafter the Chelate II/PyAOP/NMM solution was added. The resin solution mix was left bubbling overnight and a negative Kaisertest demonstrated 100% conversion to the conjugated peptide. Subsequent to cleavage and lyophilisation the crude peptide was analysed by LC-MS (20-40% B in 20 min). The analysis demonstrated that the correct MW was present, but also a large proportion of a deletion peptide (probably -Leu) was observed. RT: 13.7 min.

The crude peptide mix was purified using a 20-35% B in 40 min gradient. Several fractions were collected, analysed and lyophilised. Yield: 5.8 mg of white fluffy solid. HPLC purity: 98%. ESI-MS: Theoretical MW: 1940.40. Obtained $(M+H)^{2+}/2$: 971.2

(b) Radiolabelling of Precursor 1

The imaging agent was formed by the addition of 20 μg of the precursor in 20 μl MeOH to a vial which had been allowed to warm up to room temperature with the following reagents:

| Reagent | Quantity (mg) |
|---|---|
| $SnCl_2 \cdot 2H_2O$ | 0.016 |
| $MDP(H_4)$ | 0.025 |

| Reagent | Quantity (mg) |
|---|---|
| $NaHCO_3$ | 4.5 |
| $Na_2CO_3$ | 0.6 |
| $NaOAc \cdot 3H_2O$ | 0 |
| NaPABA | 0.200 |

1 mL of Drytec™ $^{99m}$Tc eluate (0.7-1.6 GBq) was added to the vial, the solution was allowed to stand at room temperature for 20 min and then analysed by HPLC and ITLC.

HPLC analysis was carried out using a Phenomenex Gemini column ($C_{18}$ 150×4.6 mm, 5 μm) Solvent A=0.06% ammonia and solvent B=MeCN. Dual UV were measured at 225 and 254 nm.

| HPLC gradient: Flow 1.00 ml/minute | |
|---|---|
| 0 min | 20% B |
| 20 min | 40% B |
| 22 min | 95% B |
| 26 min | 95% B |
| 27 min | 20% B |
| 30 min | 20% B |

ITLC–ITLC SG strips–mobile phase=saline or 2-butanone (MEK)

Example 5

Synthesis of Imaging Agent 3

(a) Synthesis of Precursor 3

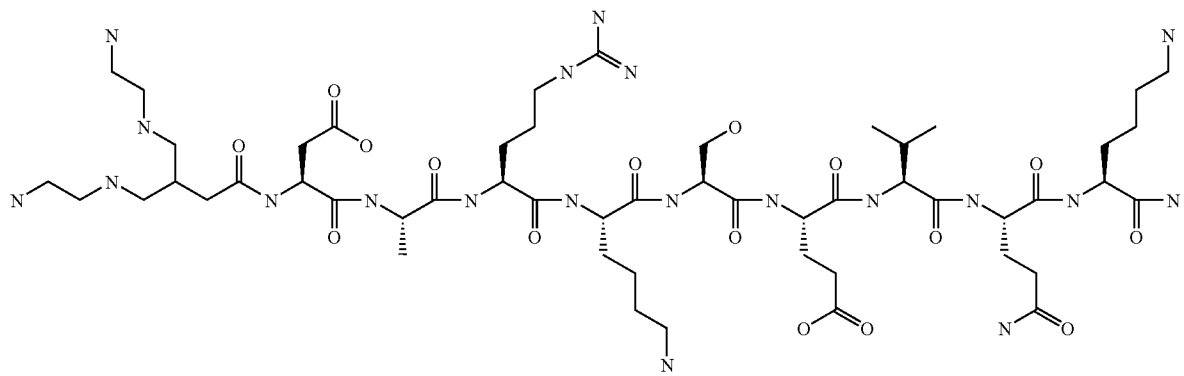

The peptide was assembled as described for Imaging Agent 1 in Example 4 above.

Subsequent to the automatic assembly the peptide resin (110 mg, 0.05 mmole) was swollen for 10 min in DMF. TetraBoc-Chelate II NHS ester (148 mg, 0.2 mmole; Boc-protected Chelate II described in Example 3) was mixed with PyAOP (104 mg, 0.2 mmole) and NMM (40 μl, 0.4 mmole) in DMF (5 ml) for 3 min. NMM (20 μl, 0.2 mmol) was added to the resin and thereafter the Chelate II/PyAOP/NMM solution was added. The resin solution mix was left bubbling overnight and a negative Kaisertest demonstrated 100% conversion to the conjugated peptide. Subsequent to cleavage and lyophilisation the crude peptide was analysed by LC-MS (2-12% B in 20 min). The analysis demonstrated that the correct MW was present as a major peak. RT: 12 min.

The crude peptide mix was purified using a 2-10% B in 40 min gradient. Three fractions were collected, analysed and lyophilised to yield 3 mg of pure peptide. Initial HPLC analysis when dissolving the peptide in pure H$_2$O demonstrated two baseline separated peaks due to differently charged species present. The peptide was then dissolved in 0.1% TFA/H$_2$O and one peak with the correct mass was obtained. HPLC purity: 98%.

Theoretical MW: 1259.49. Obtained (M+H)$^{2+}$/2: 630.6.

(b) Radiolabelling of Precursor 3

Radiolabelling was carried out according to the method described above for Imaging Agent 1, but using 50 μg of precursor, and HPLC as follows:

| HPLC gradient: Flow 1.00 ml/minute | |
|---|---|
| 0 min | 5% B |
| 10 min | 40% B |
| 15 min | 40% B |
| 17 min | 10% B |
| 20 min | 5% B |

Example 6

Synthesis of Imaging Agent 8

(a) Synthesis of Precursor 8

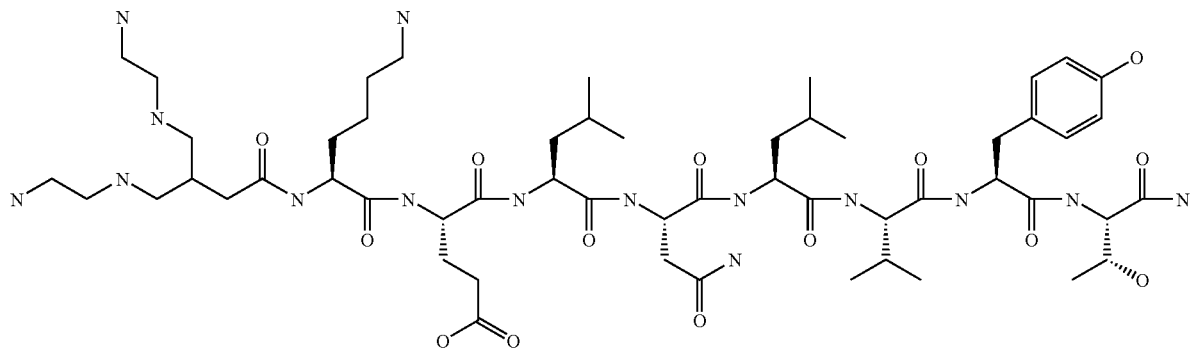

The peptide was assembled as described for Imaging Agent 1 in Example 4 above.

Subsequent to the automated assembly the peptide resin (133 mg, 0.05 mmole) was swollen in DMF for 10 min. TetraBoc-Chelate II-NHS ester (148 mg, 0.2 mmole), PyAOP (104 mg, 0.2 mmole) was dissolved in DMF, mixed and NMM (40 μl, 0.4 mmole) was added to the solution and left standing for 2 min. NMM (20 μl, 0.2 mmole) was added to the resin and thereafter the Chelate II/PyAOP/NMM solution was added. The resin mix was left with N$_2$ bubbling for 24 h, and then a Kaiser test demonstrated that the reaction had gone to completion. Subsequent to DMF/DCM washes the resin was cleaved in TFA/TIS/H$_2$O (10:0.25:0.25) for 2 h then filtrated, triturated in diethylether, rotavapory evaporated and lyophilised. The crude peptide was analysed by LC-MS (10-30% B in 20 min). The analysis demonstrated the presence of one main peak. The crude peptide mix was purified using prep HPLC (10-30% B in 40 min). Two fractions were collected, analysed and lyophilised. Yield: 8.7 mg of white fluffy solid. HPLC purity: 99%. ESI-MS: Theoretical MW: 1178.45. Obtained (M+H)$^{2+}$/2: 590.0.

(b) Radiolabelling of Precursor 8

Radiolabelling was carried out according to the method described in Example 4 for Imaging Agent 1, with HPLC as follows:

| HPLC gradient | |
|---|---|
| 0 min | 10% B |
| 20 min | 30% B |
| 21 min | 95% B |
| 26 min | 95% B |

| HPLC gradient | |
| --- | --- |
| 27 min | 10% B |
| 30 min | 10% B |

Example 7

Synthesis of Imaging Agent 10

(a) Synthesis of Precursor 10

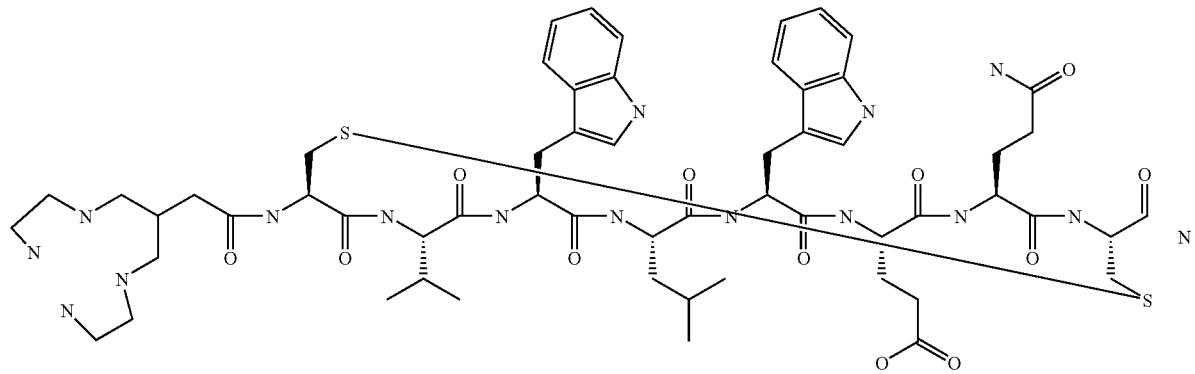

The peptide was assembled as described for Imaging Agent 1 in Example 4 above.

The peptidyl-resin H-Cys(Acm)-Val-Trp(Boc)-Leu-Trp(Boc)-Glu(OtBu)-Gln(Trt)-Cys(Acm)-R was treated with a solution of 2.5% water and 2.5% TIS in TFA (10 mL) for 2 hours. The resin was removed by filtration and the filtrate evaporated in vacuo. Diethyl ether was added to the residue. The resulting precipitate was washed with diethyl ether and air-dried affording 84 mg crude H-Cys(Acm)-Val-Trp-Leu-Trp-Glu-Gln-Cys(Acm)-NH₂.

Crude H-Cys(Acm)-Val-Trp-Leu-Trp-Glu-Gln-Cys(Acm)-NH₂ (84 mg) was dissolved in 75% aqueous AcOH (80 mL) under a blanket of argon. 1 M HCl (8 mL), anisole (0.4 mL) and 0.025 M I2 in AcOH (26.6 mL) were added in that order. After half an hour, 1 M ascorbic acid was added in order to quench the reaction. Most of the solvents were evaporated in vacuo. The residue was diluted with water/0.1 TFA and the product purified twice by preparative HPLC affording 17 mg pure Cys 1-8; H-Cys-Val-Trp-Leu-Trp-Glu-Gln-Cys-NH₂.

Cys 1-8; H-Cys-Val-Trp-Leu-Trp-Glu-Gln-Cys-NH₂ (17 mg), tetra-Boc-Chelate II NHS ester (17 mg), 1-hydroxy-7-azabenzotriazole (HOAt) (3 mg) and N-methylmorpholine (17 μl) were dissolved in DMF (1 mL) and the reaction mixture stirred at room temperature overnight. The mixture was then diluted with 60% ACN/water/0.1% TFA (7 mL) and the product purified by preparative HPLC affording 16 mg pure Cys 1-8; tetra-Boc-Chelate II-Cys-Val-Trp-Leu-Trp-Glu-Gln-Cys-NH₂.

Cys 1-8; tetra-Boc-Chelate II-Cys-Val-Trp-Leu-Trp-Glu-Gln-Cys-NH₂ was treated with a solution of 2.5% water and 2.5% TIS in TFA (10 mL) for 2 hours. TFA was evaporated in vacuo and the residue dissolved in DMF (0.5 mL) and diluted with 20% ACN/water/0.1% TFA (5 mL) and the product purified by preparative HPLC (gradient: 20-40% B over 40 minutes where A=H₂O/0.1% TFA and B=ACN/0.1% TFA, flow rate: 10 ml/minute, column: Phenomenex Luna™ 5μ C18 (2) 250×21.20 mm, detection: UV 214 nm, product retention time: 24.7 minutes) affording 8.7 mg pure Cys 1-8; Chelate II-Cys-Val-Trp-Leu-Trp-Glu-Gln-Cys-NH₂). The product was characterised using mass spectrometry (MH⁺ calculated: 1263.6, MH⁺. found: 1263.8).

(b) Radiolabelling of Precursor 10

Radiolabelling was carried out according to the method described in Example 4 for Imaging Agent 1, but using 50 μg of the precursor.

Example 8

Synthesis of Imaging Agent 29

(a) Synthesis of Precursor 29

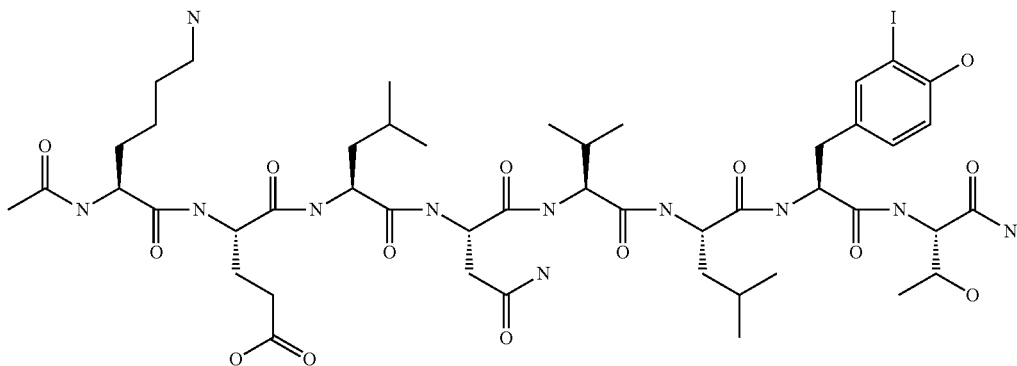

The peptide was assembled as described for Imaging Agent 1 in Example 4 above.

Subsequent to the automated assembly the peptide resin (65 mg, 0.025 mmole) was swollen in DMF for 10 min. The resin was thereafter acetylated using; Ac$_2$O (450 µl)/DIEA (250 µl)/HOBt in DMP (10 ml) for 2 h. A negative Kaisertest demonstrated complete acetylation. Due to the concomitant esterification of the (3I)Y—OH, the resin was treated with 20% piperidine in DMF for 2×20 min. The resin was then washed thoroughly with DMF/DCM and dried at RT. The resin was cleaved in TFA/TIS/H$_2$O (10:0.25:0.25) for 2 h then filtrated, triturated in diethylether, rotavapory evaporated and lyophilised. The crude peptide was analysed by LC-MS (20-40% B in 20 min). The analysis demonstrated the presence of two main peaks. The crude peptide mix was purified by prep HPLC (20-35% B in 40 min). Two fractions were collected, analysed and lyophilised. Yield: 0.5 mg of white solid. HPLC purity: 99%. ESI-MS: Theoretical MW: 1146.1. Obtained (M+H)$^{2+}$/2: 573.6.

(b) Radiolabelling of Precursor 29

10 µl of (1 mM, 10$^{-8}$ moles) of Na$^{127}$I in 0.05M NaOH was initially added to 200 µl 0.2 M ammonium acetate buffer at pH 4. The solution was then added to ~25 µl of Na$^{123}$I solution in 0.05 M NaOH (450 MBq) (GE Healthcare Cygne) in the Na$^{123}$I vial. The contents were transferred to a silanised vial and 10 µl peracetic acid (5 mM, 5×10$^{-8}$ moles) was added. The precursor (100 µg in 70 µl MeOH, 8.1×10$^{-8}$ moles) was then added and the contents of the vial were mixed by pipette. After approximately 5 min, the reaction mixture was analysed by H PLC.

HPLC analysis was carried out using a Phenomenex Luna™ (C$_{18}$ 150×4.6 mm, 5 µm) column. Solvent A=0.1% TFA/H$_2$O and solvent B=0.1% TFA/H$_2$O. Dual UV were measured at 225 and 254 nm.

| HPLC gradient Flow 1 ml/minute | |
|---|---|
| 0 min | 10% B |
| 20 min | 50% B |
| 22.5 min | 100% B |
| 27 min | 100% B |
| 27.5 min | 20% B |
| 31 min | 20% B |

ITLC–ITLC   SG   strips–mobile   phase=saline

Example 9

Synthesis of Imaging Agent 35

(a) Synthesis of Precursor 35

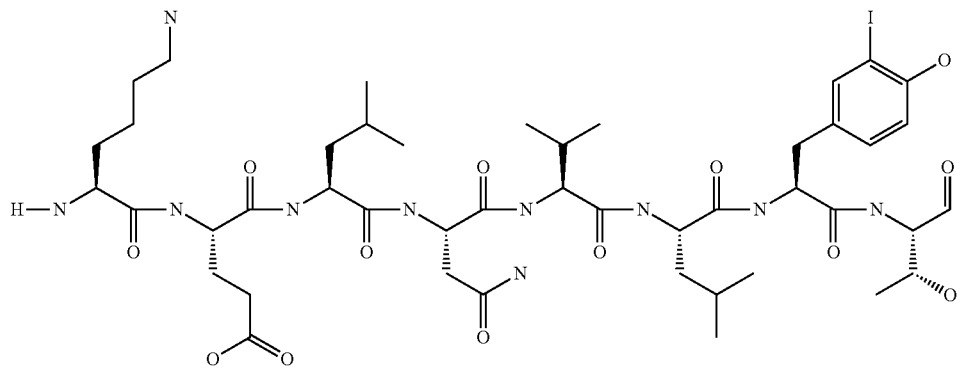

The peptide was assembled as described for Imaging Agent 1 in Example 4 above.

Subsequent to the automated assembly the peptide resin (150 mg) was cleaved in TFA/TIS/H$_2$O (10:0.25:0.25) for 2 h then filtrated, triturated in diethylether, rotavapory evaporated and lyophilised. The crude peptide was analysed by LC-MS (10-30% B in 20 min). The analysis demonstrated the presence of two main peaks. The crude peptide mix was purified using a 10-30% B in 40 min gradient. Two fractions were collected, analysed and lyophilised. Yield: 1.5 mg of white fluffy solid. HPLC purity: 99%. ESI-MS: Theoretical MW: 1104.06. Obtained (M+H)$^{2+}$/2: 552.8.

(b) Radiolabelling of Precursor 35

Radiolabelling was carried out according to the method described in Example 8 for Imaging Agent 29.

Example 10

Synthesis of Imaging Agent 36

(a) Synthesis of Precursor 36 esterification of the (3I)Y—OH, the resin was treated with 20% piperidine in DMF for 2×20 min. The resin was then washed thoroughly with DMF/DCM and dried at RT. The resin was cleaved in TFA/TIS/H$_2$O (10:0.25:0.25) for 2 h then filtrated, triturated in diethylether, rotavapory evaporated and lyophilised. The crude peptide was analysed by LC-MS (20-40% B in 20 min). The analysis demonstrated the presence of two main peaks. The crude peptide (17 mg) was oxidised in the following solution H$_2$O (24 ml) MeCN (16 ml) and DMSO (160 µl). pH was adjusted to approx. 9 by 25% NH$_3$. The solution was left stirring at RT overnight. LC-MS analysis demonstrated that the oxidation had gone to completion and the pH was adjusted to 4 by AcOH. The peptide was lyophilised and thereafter purified by prep HPLC (20-35% B in 40 min).

Two fractions were collected and analysed. Yield: 2.5 mg of white fluffy solid. HPLC purity: 99%. ESI-MS: Theoretical MW: 1350.37. Obtained (M+H)$^{2+}$/2: 675.6

(b) Radiolabelling of Precursor 36

Radiolabelling was carried out according to the method described in Example 8 for Imaging Agent 29, but with HPLC as follows:

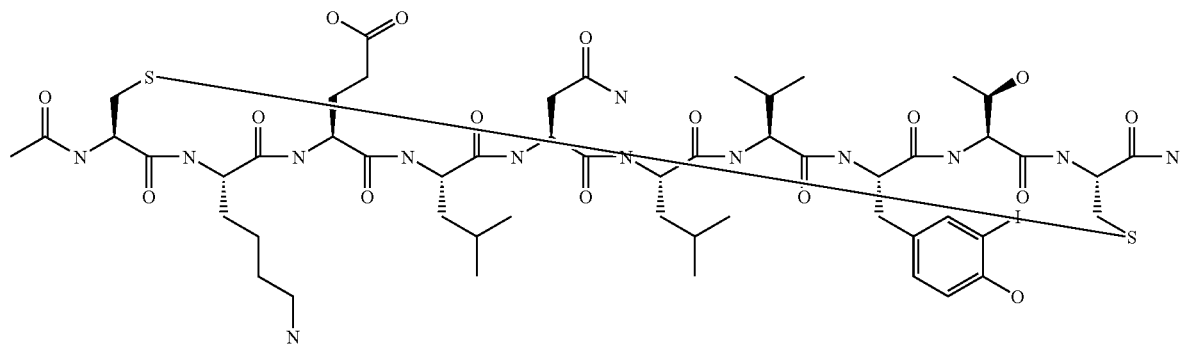

The peptide was assembled as described for Imaging Agent 1 in Example 4 above.

Subsequent to the automated assembly the peptide resin (130 mg, 0.05 mmole) was swollen in DMF for 10 min. The resin was thereafter acetylated using; Ac$_2$O (450 µl)/DIEA (250 µl)/HOBt in DMF (10 ml) for 2 h. A negative Kaisertest demonstrated complete acetylation. Due to the concomitant

| Flow 1 ml/minute | |
| --- | --- |
| 0 min | 20% B |
| 20 min | 35% B |

-continued

| | |
|---|---|
| Flow 1 ml/minute | |
| 22.5 min | 100% B |
| 27 min | 100% B |
| 27.5 min | 20% B |
| 31 min | 20% B |

Example 11

Synthesis of Imaging Agent 37

(a) Synthesis of Precursor 37

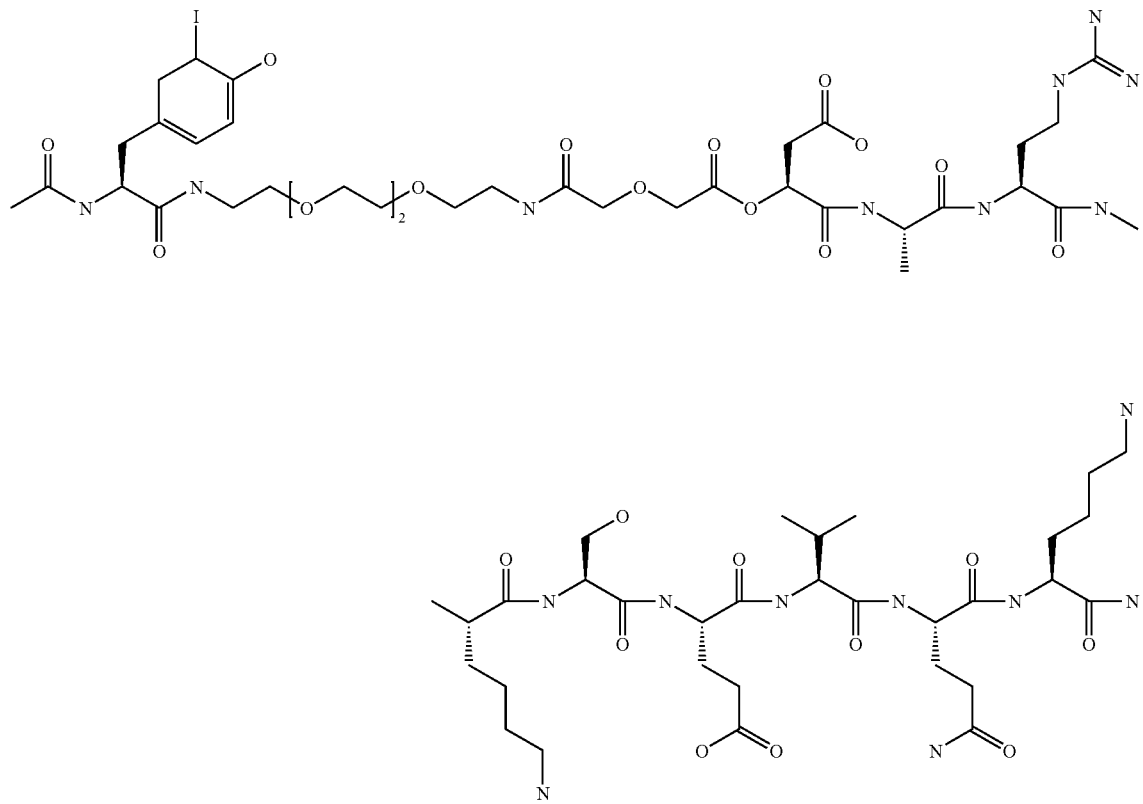

The peptide was assembled as described for Imaging Agent 1 in Example 4 above.

Subsequent to the automated assembly the peptide resin (65 mg, 0.025 mmole) was swollen in DMF for 10 min. Fmoc-PEG4-COOH (100 mg, 0.2 mmole) was dissolved in DMF and added to a PyAOP (100 mg, 0.2 mmole)/DMF solution. NMM (40 µl, 0.4 mmole) was added and the solution was left standing for 2 min. NMM (20 µl, 0.2 mmole) was added to the resin and thereafter the coupling solution was added. The resin mix was left bubbling overnight. A Kaiser demonstrated that the reaction was not complete and the coupling procedure was repeated twice to give a negative Kaisertest. Fmoc deprotection was carried out using 20% piperidine in DMF (2×7 ml) for 1×10 and 1×5 min. Fmoc-(3I)Y—COOH (0.5 mmole) was coupled using PyAOP (211 mg, 0.4 mmole)/NMM (80 µl, 0.8 mmole) in DMF for 3 h. A Kaisertest demonstrated that the reaction had gone to completion.

Subsequent to DMF wash, the resin was acetylated using; Ac$_2$O (450 µl)/DIEA (250 µl)/HOBt in DMP (10 ml) for 2 h. A negative Kaisertest demonstrated complete acetylation. Due to the concomitant esterification of the (3I)Y—OH, the resin was treated with 20% piperidine in DMF for 2×20 min. The resin was then washed thoroughly with DMF/DCM and dried at RT. The resin was cleaved in TFA/TIS/H$_2$O (10:0.25:0.25) for 2 h then filtrated, triturated in diethylether, rotavapory evaporated and lyophilised. The crude peptide was analysed by LC-MS (20-40% B in 20 min) and demonstrated one main peak in approximately 90% purity. As the peptide was only to be used as a cold standard the crude peptide was not purified further. ESI-MS: Theoretical MW: 1681.6 Obtained (M+H)$^{2+}$/2: 840.3.

(b) Radiolabelling of Precursor 37

Radiolabelling was carried out according to the method described in Example 8 for Imaging Agent 29, but with HPLC gradient as follows:

| | |
|---|---|
| 0 min | 5% B |
| 20 min | 25% B |
| 22.5 min | 100% B |
| 27 min | 100% B |
| 27.5 min | 25% B |
| 31 min | 5% B |

Example 12

Synthesis of Imaging Agent 38

(a) Synthesis of Precursor 38

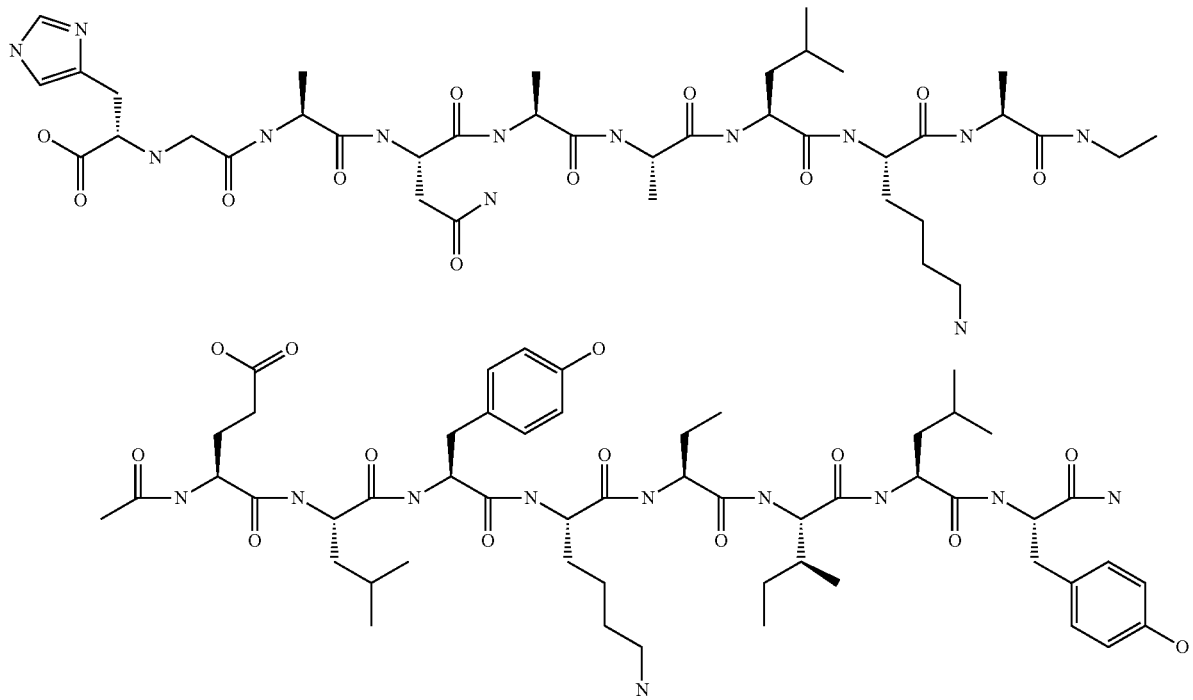

The peptide was assembled as described for Imaging Agent 1 in Example 4 above.

Subsequent to the automated assembly the peptide resin (80 mg, 0.03 mmole) was swollen for 10 min in DMF. Bromoacetic acid (250 mg,) and DCC (200 mg,) was mixed and DCM (10 ml) was added. The slurry was left stirring for 1 h at RT and thereafter filtered. The DCM solution was rotavapory evaporated and DMF (10 ml) was added to the residue. Thereafter DIEA (50 µl, 0.5 mmole) was added and the DMF/DIEA solution was added to the resin. The resin mix was left bubbling for 90 min and a negative Kaisertest demonstrated that the reaction had gone to completion. After DMF wash His (trt)OtBu (100 mg, 0.3 mmole) in DMF and DIEA (50 µl, 0.5 mmole) was added to the resin. The resin mix was left bubbling overnight. The resin was washed thoroughly with DMF/DCM and left at RT overnight. The resin was cleaved in TFA/TIS/$H_2O$ (10:0.25:0.25) for 2 h then filtrated, triturated in diethylether, rotavapory evaporated and lyophilised. The crude peptide was analysed by LC-MS (20-40% B in 20 min). The analysis demonstrated the presence of two main peaks. The crude peptide mix was purified by prep HPLC (20-35% B in 40 min). One fraction was collected, analysed and lyophilised. Yield: 2 mg of white solid. HPLC purity: 98%. ESI-MS: Theoretical MW: 1917.3. Obtained $(M+H)^{2+}/2$: 958.8.

(b) Radiolabelling of Precursor 38

1 ml of $^{99m}TcO_4^-$ eluted from a generator was added to a Tc-carbonyl kit (Isolink™ Mallinckrodt, Petten, Netherlands), 5 ml of headspace was removed and the vial was heated at 100° C. for 20 min. The vial was cooled to room temperature, 1 ml of 0.1M PBS (pH 7.4) was added, the pH of the solution was measured and then analysed by TLC (Merck Silica Gel–mobile phase=99% MeOH/1% HCl).

200 µl of the $^{99m}Tc(CO)_3(H_2O)_3$ solution was added to a new silanised vial, together with 50 µl/50 µg of precursor in MeOH and 200 µl 1M 2-(N-morpholino)ethanesulfonic acid buffer at pH 6.5. The solution was heated at 60° C. for 60 min and then analysed by HPLC and ITLC (SG strips–mobile phase=saline).

Initial HPLC analyses carried out using a Phenomenex Gemini column ($C_{18}$ 150×4.6 mm, 5 µm), solvent A=0.1% TFA/$H_2O$, solvent B=0.1% TFA/MeCN. UV measured at 254 nM.

| HPLC gradient: Flow 1 ml/minute | |
|---|---|
| 0 min | 20% B |
| 20 min | 40% B |
| 21 min | 95% B |
| 26 min | 95% B |
| 27 min | 20% B |
| 32 min | 20% B |

Subsequent HPLC analyses were carried out using either a Phenomenex Gemini $C_{18}$ column 150×2.1 mm (5 µm)-Flow rate 0.2 ml/min for analyses or a Phenomenex Gemini $C_{18}$ column 150×4.6 mm (3 µm)-Flow rate 1.0 ml/min for purifications.

Solvent A=0.06% ammonia and solvent B=MeCN. UV was measured at 214 nm.

| HPLC gradient: | |
|---|---|
| 0 min | 25% B |
| 20 min | 95% B |
| 26 min | 95% B |

47

-continued

| HPLC gradient: | |
|---|---|
| 27 min | 25% B |
| 30 min | 25% B |

Example 13

Synthesis of Imaging Agent 39

(a) Synthesis of Precursor 39

48 analysed and lyophilised. Yield: 1 mg of white solid. HPLC purity: 98%. ESI-MS: Theoretical MW: 1857.2. Obtained $(M+H)^{2+}/2$: 929.5.

(b) Radiolabelling of Precursor 39

50 µl/50 µg of precursor (in MeOH) was added to a silanised vial. 0.3 ml of tricine (30 mg in 0.1% ammonium acetate buffer pH 5) was then added to the vial followed by 1 ml 0.1% ammonium acetate buffer (pH 5). 0.5 ml $^{99m}TcO_4^-$ (activity 0.7-4.4 GBq) was then added to the vial followed by 0.1 ml $N_2$ purged $SnCl_2$ saline solution (0.44 mM dm$^{-3}$). This was left to react at room temperature for 30 min.

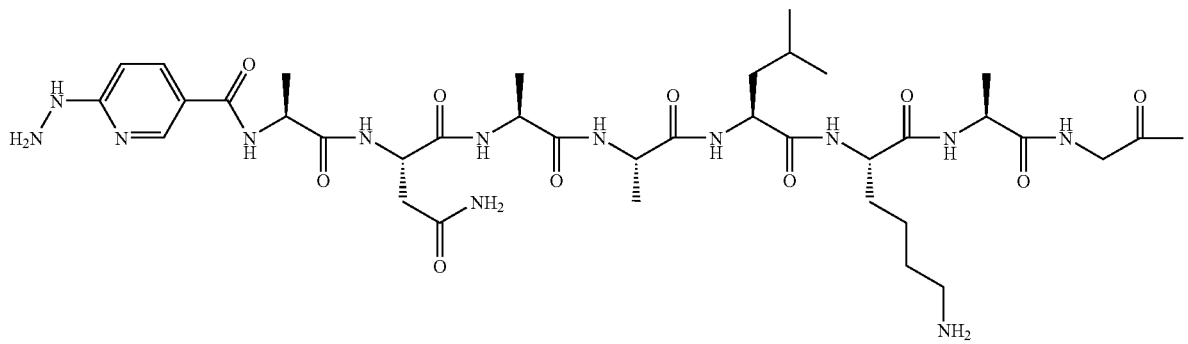

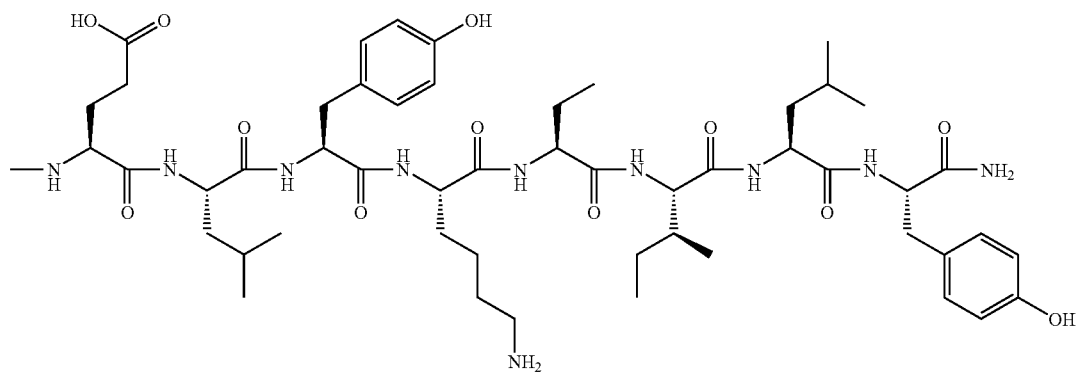

The peptide was assembled as described for Imaging Agent 1 in Example 4 above.

Subsequent to the automated assembly the peptide resin (13 mg, 0.01 mmole) was transferred to a Microwave vial and Boc-HYNIC-NHS ester (5 mg, 0.015 mmole)/HOBt (2 mg, 0.015 mmole)/DIEA (8 µl, 0.0.6 mmole) in DMF (3 ml) was added. The resin mix was left standing for 15 min at RT and thereafter placed in a microwave for 2 h at 60° C. The resin was cleaved in TFA/TIS/H$_2$O (10:0.25:0.25) for 2 h then filtrated, triturated in diethylether, rotavapory evaporated and lyophilised. The crude peptide was analysed by LC-MS (20-40% B in 20 min). The analysis demonstrated the presence of two main peaks. The crude peptide mix was purified by prep HPLC (20-35% B in 40 min). One fraction was collected, HPLC analysis was carried out using a Phenomenex Gemini column (C$_{18}$ 150×4.6 mm, 5 µm) Solvent A=10 mM phosphate buffer pH 6 and solvent B=MeCN. UV was measured at 254 nm.

| HPLC gradient: Flow 1 ml/minute | |
|---|---|
| 0 min | 20% B |
| 20 min | 40% B |
| 21 min | 95% B |
| 26 min | 95% B |
| 27 min | 20% B |
| 32 min | 20% B |

ITLC SG strips–mobile phase=saline

Example 14

Synthesis of Imaging Agent 40

(a) Synthesis of Precursor 40

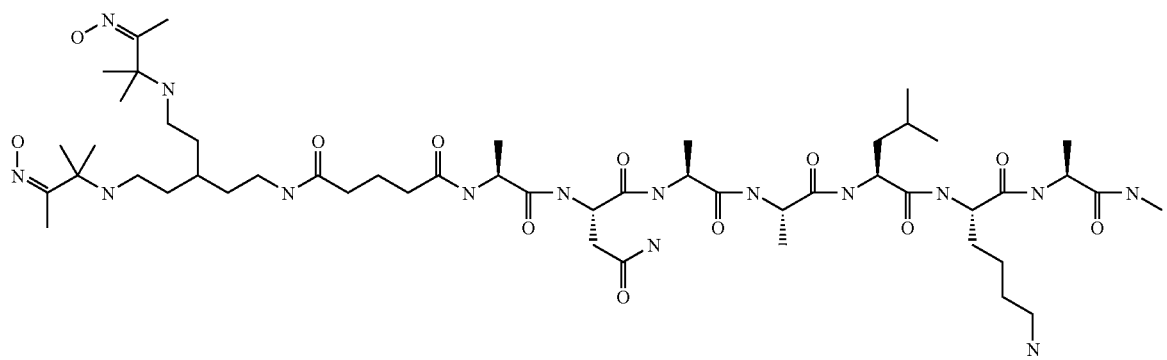

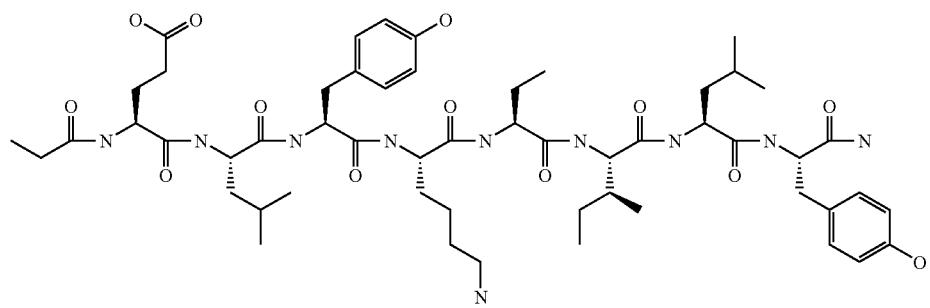

The peptide was assembled as described for Imaging Agent 1 in Example 4 above.

Subsequent to the automated assembly the peptide resin (ivDde protection on Lysine) (182 mg, 0.1 mmole) was cleaved in TFA/TIS/H$_2$O (10:0.25:0.25) for 2 h then filtrated, triturated in diethylether, rotavapory evaporated and lyophilised. Chelate I-glutaric acid (23 mg), PyAOP (25 mg), NMM (6 µl) was dissolved in DMF (3 ml) and added to the peptide residue. The solution was left shaking at RT overnight. The crude peptide was analysed by LC-MS (25-70% B in 20 min). The analysis demonstrated the presence of two main peaks. The crude peptide mix (Lysine protected) was purified by prep HPLC (30-60% B in 40 min). Three fractions were collected, analysed and lyophilised. Yield:

4.3 mg of white solid. HPLC purity: 98%. The ivDde protecting groups were removed by dissolving the peptide (4 mg) in DMF (8 ml) and adding Hydrazinehydrate (160 µl). The deprotection was monitored by HPLC, and after 20 min the reaction had gone to completion. The sample was diluted with 10% MeCN/H$_2$O and the pH was adjusted to 4. Thereafter the peptide was purified by HPLC (20-40% B in 40 min) and lyophilised to yield 2.5 mg of white fluffy solid. HPLC purity: 98%. ESI-MS: Theoretical MW: 2161.7. Obtained (M+H)$^{2+}$/2: 1082.2.

(b) Radiolabelling of Precursor 40

Radiolabelling was carried out as described in Example 4 for Imaging Agent 1, for 20 minutes at room temperature, with the following HPLC gradient:

| Flow 1.00 ml/minute | |
|---|---|
| 0 min | 25% B |
| 20 min | 60% B |
| 21 min | 95% B |
| 27 min | 25% B |
| 32 min | 25% B |

Example 15

Synthesis of Imaging Agent 41

(a) Synthesis of Precursor 41

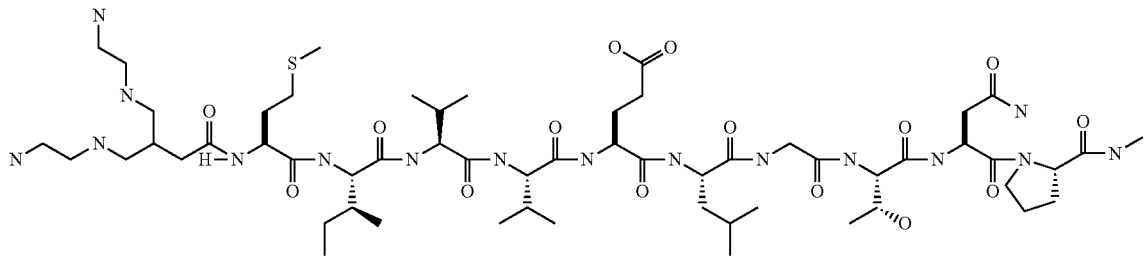

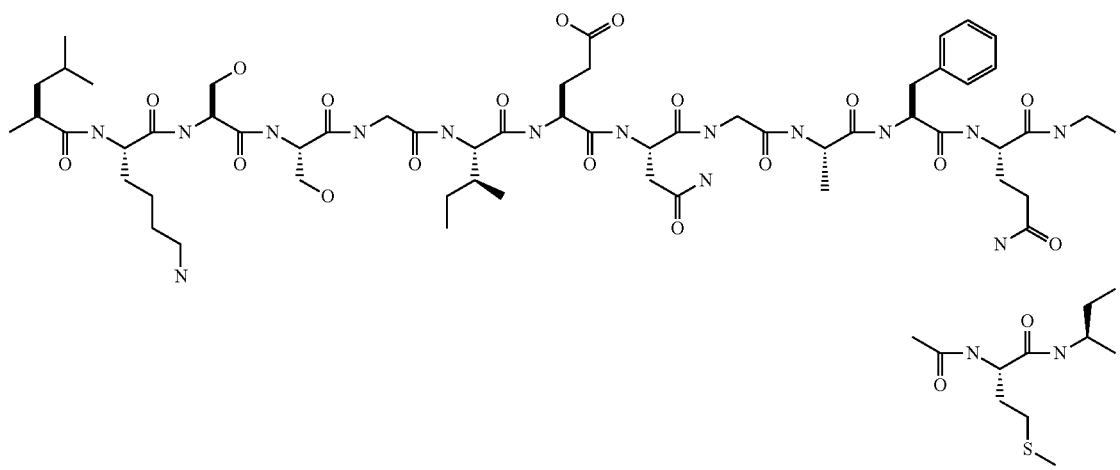

The peptide was assembled as described for Imaging Agent 1 in Example 4 above.

Subsequent to the automated assembly the peptide resin (70 mg, 0.03 mmole) was swollen for 10 min in DMF. Tetra-Boc-Chelate II NHS ester (70 mg, 0.1 mmole; Boc-protected Chelate II described in Example 3) was mixed with PyAOP (50 mg, 0.1 mmole) and NMM (30 µl, 0.3 mmole) in DMF (5 ml) for 3 min. NMM (20 µl, 0.2 mmol) was added to the resin and thereafter the Chelate II/PyAOP/NMM solution was added. The resin solution mix was left bubbling overnight and a negative Kaisertest demonstrated 100% conversion to the conjugated peptide. The peptide was cleaved in TFA/TIS/H$_2$O (10:0.25:0.25) for 2 h then filtrated, triturated in diethylether, rotavapory evaporated and lyophilised. LC-MS (20-40% B in 20 min) demonstrated one main peak and the crude peptide was purified by prep HPLC (20-30% B in 40 min). One fraction was collected and yielded 1 mg of white solid after lyophilisation. HPLC purity: 98%. ESI-MS: Theoretical MW: 2948.6. Obtained (M+H)$^{3+}$/3: 983.4.

(b) Radiolabelling of Precursor 41

Radiolabelling was carried out as described in Example 4 for Imaging Agent 1, with 50 µg of precursor, for 20 minutes, at room temperature, with the following HPLC gradient:

| | |
|---|---|
| 0 min | 20% B |
| 20 min | 40% B |
| 21 min | 95% B |
| 26 min | 95% B |
| 27 min | 20% B |
| 32 min | 20% B |

Example 16

Synthesis of Imaging Agent 42

(a) Synthesis of Precursor 42

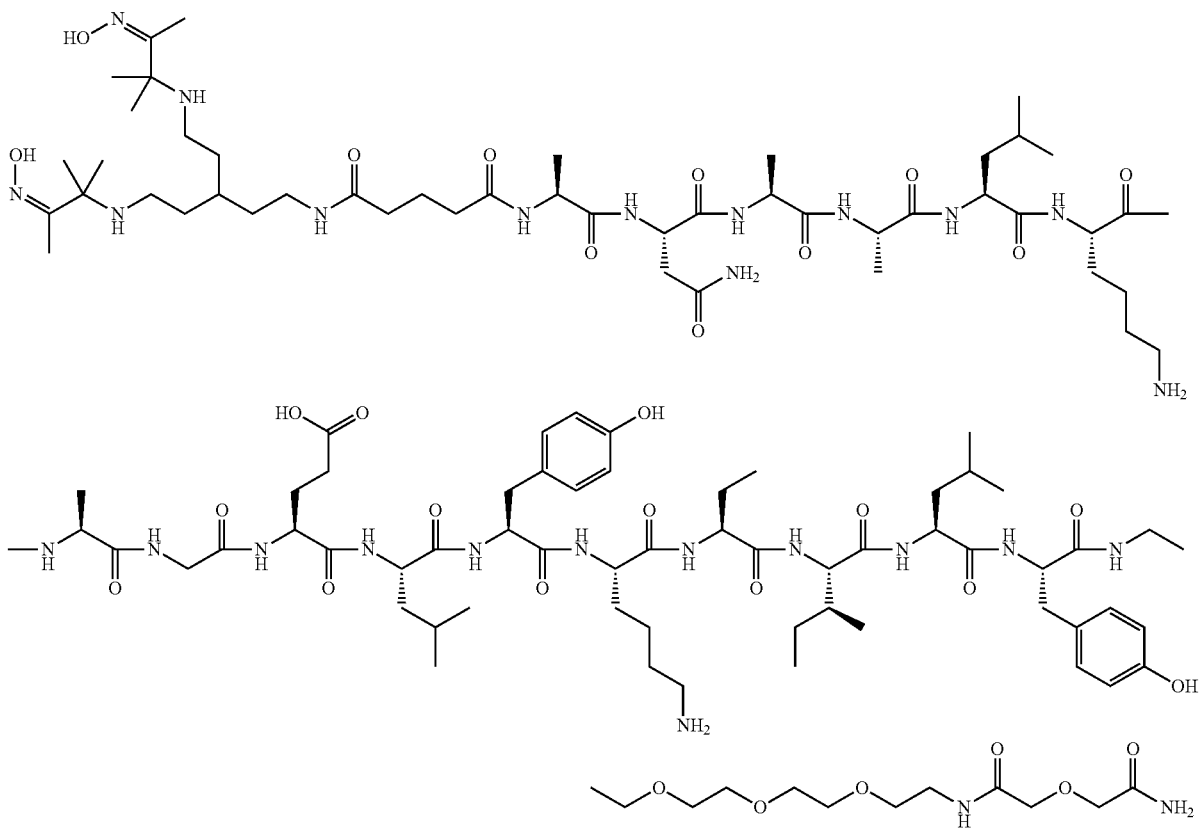

MW = 2452.0
EM = 2450.5
MF - C115H195N27O31

The peptide was assembled as described for Imaging Agent 1 in Example 4 above.

The peptidyl-resin (0.05 mmol) was treated with a solution of 2.5% water and 2.5% triisopropylsilane (TIS) in TFA (5 mL) for 2 hours. The resin was removed by filtration and the filtrate evaporated in vacuo. Diethyl ether was added to the residue. The resulting precipitate was washed with ether and air-dried affording 95 mg crude H-Ala-Asn-Ala-Ala-Leu-Lys(ivDde)-Ala-Gly-Glu-Leu-Tyr-Lys(ivDde)-Abu-Ile-Leu-Tyr-PEG(4)-diglycoloyl-NH$_2$.

H-Ala-Asn-Ala-Ala-Leu-Lys(ivDde)-Ala-Gly-Glu-Leu-Tyr-Lys(ivDde)-Abu-Ile-Leu-Tyr-PEG(4)-diglycoloyl-NH$_2$ (24 mg), Chelate 1-Glut active ester (62 mg), 1-hydroxy-7-azabenzotriazole (HOAt) (7 mg) and sym.-collidine (66 μL) were dissolved in 1-methyl-2-pyrrolidinone (NMP) (1 mL) and the reaction mixture stirred at 37° C. over night. The reaction mixture was diluted with NMP (0.5 mL), water/0.1% TFA (1 mL) and acetonitrile (ACN)/0.1% TFA (1 mL) and the product purified using preparative HPLC affording 5 mg pure Chelate 1-Glut-Ala-Asn-Ala-Ala-Leu-Lys(ivDde)-Ala-Gly-Glu-Leu-Tyr-Lys(ivDde)-Abu-Ile-Leu-Tyr-PEG(4)-diglycoloyl-NH$_2$.

Chelate 1-Ala-Asn-Ala-Ala-Leu-Lys(ivDde)-Ala-Gly-Glu-Leu-Tyr-Lys(ivDde)-Abu-Ile-Leu-Tyr-PEG(4)-diglycoloyl-NH$_2$ (5 mg) was treated with 2% hydrazine monohydrate/NMP (1 mL) for 30 minutes. 10% ACN/water/0.1% TFA (4 mL) was added to the reaction mixture and the product purified by preparative HPLC (gradient: 10-40% B over 40 minutes where A=H$_2$O/0.1% TFA and B=ACN/0.1% TFA, flow rate: 10 mL/minute, column: Phenomenex Luna™ 5μ C18 (2) 250×21.20 mm, detection: UV 214 nm, product retention time: 35.0 min) affording 2.3 mg pure product. The pure product was analysed by analytical HPLC (gradient: 10-40% B over 5 minutes where A=H$_2$O/0.1% TFA and B=ACN/0.1% TFA, flow rate: 0.3 mL/minute, column: Phenomenex Luna™ 3μ C18 (2) 20×2 mm, detection: UV 214 nm, product retention time: 4.02 min). Further product characterisation was carried out using mass spectrometry (MH$_2^{2+}$ calculated: 1226.3, MH$_2^{2+}$. found: 1226.3).

(b) Radiolabelling of Precursor 42

Radiolabelling was carried out as described in Example 4 for Imaging Agent 1, for 20 minutes at room temperature, with the following HPLC gradient:

| Flow 1.00 ml/minute | |
|---|---|
| 0 min | 25% B |
| 20 min | 60% B |
| 21 min | 95% B |
| 27 min | 25% B |
| 32 min | 25% B |

Example 17

Synthesis of Imaging Agent 43

(a) Synthesis of Precursor 43

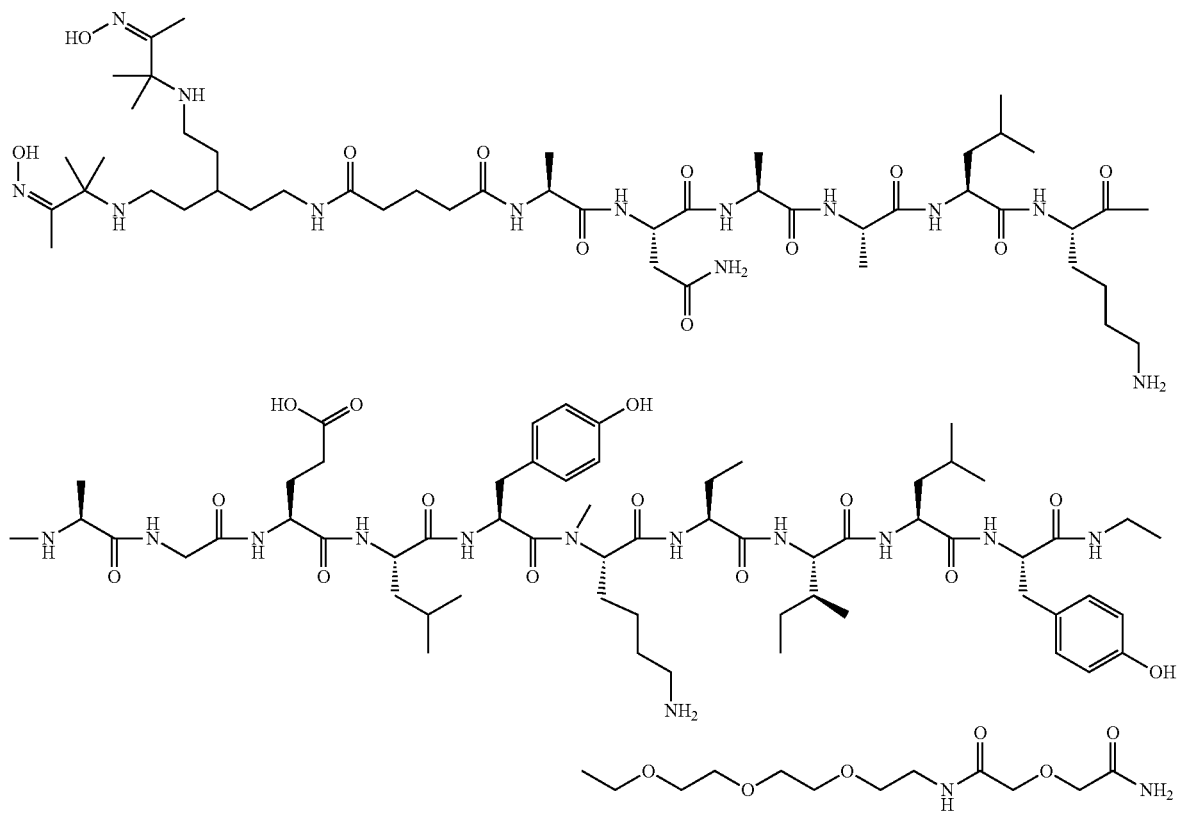

MW = 2466.0
EM = 2464.5
MF = C116H197N27O31

The peptide was assembled as described for Imaging Agent 1 in Example 4 above.

The peptidyl-resin (0.05 mmol) was treated with a solution of 2.5% water and 2.5% TIS in TFA (5 mL) for 2 hours. The resin was removed by filtration and the filtrate evaporated in vacuo. Diethyl ether was added to the residue. The resulting precipitate was washed with ether and air-dried affording 77 mg crude H-Ala-Asn-Ala-Ala-Leu-Lys(ivDde)-Ala-Gly-Glu-Leu-Tyr-N-Me-Lys(ivDde)-Abu-Ile-Leu-Tyr-PEG(4)-diglycoloyl-NH$_2$.

H-Ala-Asn-Ala-Ala-Leu-Lys(ivDde)-Ala-Gly-Glu-Leu-Tyr-N-Me-Lys(ivDde)-Abu-Ile-Leu-Tyr-PEG(4)-diglycoloyl-NH$_2$ (24 mg), Chelate I Glut active ester (62 mg), 1-hydroxy-7-azabenzotriazole (HOAt) (7 mg) and sym.-collidine (66 μL) were dissolved in NMP (1 mL) and the reaction mixture stirred at 37° C. over night. The reaction mixture was diluted with NMP (0.5 mL), water/0.1% TFA (1 mL) and ACN/0.1% TFA (1 mL) and the product purified using preparative HPLC affording 6.5 mg pure Chelate 1-Glut-Ala-Asn-Ala-Ala-Leu-Lys(ivDde)-Ala-Gly-Glu-Leu-Tyr-N-Me-Lys(ivDde)-Abu-Ile-Leu-Tyr-PEG(4)-diglycoloyl-NH$_2$.

Chelate 1-Ala-Asn-Ala-Ala-Leu-Lys(ivDde)-Ala-Gly-Glu-Leu-Tyr-N-Me-Lys(ivDde)-Abu-Ile-Leu-Tyr-PEG(4)-diglycoloyl-NH$_2$ (6.5 mg) was treated with 2% hydrazine monohydrate/NMP (1 mL) for 35 minutes. 10% ACN/water/ 0.1% TFA (8 mL) was added to the reaction mixture and the product purified by preparative HPLC (gradient: 10-40% B over 40 minutes where A=H$_2$O/0.1% TFA and B=ACN/0.1% TFA, flow rate: 10 mL/minute, column: Phenomenex Luna™ 5μ C18 (2) 250×21.20 mm, detection: UV 214 nm, product retention time: 31.0 min) affording 5.3 mg pure product. The pure product was analysed by analytical HPLC (gradient: 10-40% B over 5 minutes where A=H$_2$O/0.1% TFA and B=ACN/0.1% TFA, flow rate: 0.3 mL/minute, column: Phenomenex Luna™ 3μ C18 (2) 20×2 mm, detection: UV 214 nm, product retention time: 3.52 min). Further product characterisation was carried out using mass spectrometry (MH$_2^{2+}$ calculated: 1233.3, MH$_2^{2+}$. found: 1233.3).

(b) Radiolabelling of Precursor 43

Radiolabelling was carried out as described in Example 4 for Imaging Agent 1, for 20 minutes at room temperature, with the following HPLC gradient:

| Flow 1.00 ml/minute | |
|---|---|
| 0 min | 20% B |
| 20 min | 55% B |
| 21 min | 95% B |
| 27 min | 20% B |
| 32 min | 20% B |

Example 18

In Vitro Binding of Imaging Agent 1 to Collagen Type I

A Maxisorp plate was incubated overnight at 4° C. with 50 µL or 100 µL 0.1 mg/mL collagen type I. All solutions were removed from the wells using a pipette. Wells were washed twice with 200 µL PBS, and then incubated with 150 µL PBS containing 0.1% BSA for 30 minutes at room temperature. Wells were washed five times with 200 µL PBS, and then 90 µL PBS was added to each well. 10 µL of neat (and two-fold serially diluted in PBS) Imaging Agent 1 was added to the wells in quadruplicate. The plate was sealed and incubated for 1 hour at 37° C.

The wells were washed seven times with ice-cold PBS (200 µL); and then the wells were transferred to a glass vial and counted (measured) for $^{99m}$Tc-activity using a Wallac counter for a 60 s count for each sample.

FIG. 1 illustrates binding of Imaging Agent 1 to collagen type I coated wells from one experiment. The curve (black trace) was fitted using a non-linear regression one-site binding hyperbola modelled with GraphPad PRISM and derived $B_{max}$=1068 attomoles and $K_d$=194.2 nM using the fitted data ($r^2$=0.9992).

Example 19

In Vivo Biodistribution of Imaging Agent 1

18 Male Sprague Dawley rats (180-200 g) were operated upon. Each animal's abdomen was shaved and swabbed with betadine solution followed by 5 mg/kg carprofen s.c and 5 mg/kg buproprophine s.c. Under Isoflurane anaesthesia a mid-line laparotomy was performed and the common bile duct located. Bile duct was double ligated (n=9). The first ligation made between the junction of the hepatic ducts and the second above the entrance of the pancreatic ducts. Before closing ~2-3 ml saline was administered into the peritoneum. Fascia and skin were closed and animals were administered with 2 mg/kg metaclopromide s.c, 5 mg/kg Baytril s.c., and ~2 ml saline s.c.

Carprofen was given (5 mg/kg) as required over the next couple of days. Control animals underwent sham surgery where bile duct was manipulated and a suture passed under the bile duct (n=9). Animals were closely monitored for 15 days. On day 16 post surgery under isoflurane anaesthesia animals were injected with 0.1 ml Imaging Agent 1 i.v. via tail vein (~1 MBq). Organs were dissected at 5, 60 & 120 min post-injection (BDL animals). Organs were dissected at 5, 60 & 120 min (Sham animals).

The table below shows the percentage injected dose at the various timepoints studied.

|  | 2 minutes | | 5 minutes | | 30 minutes | | 60 minutes | | 120 minutes | |
| --- | --- | --- | --- | --- | --- | --- | --- | --- | --- | --- |
|  | BDL | Sham | BDL | Sham | BDL | Sham | BDL | Sham | BDL | Sham |
| Bone | 3.9 | 2.9 | 3.0 | 3.0 | 0.8 | 0.3 | 0.3 | 0.1 | 0.3 | 0.1 |
| Muscle | 18.5 | 16.1 | 19.0 | 16.6 | 3.9 | 1.6 | 1.6 | 0.5 | 1.1 | 0.2 |
| Blood | 21.4 | 14.5 | 15.5 | 11.3 | 3.2 | 1.1 | 1.2 | 0.4 | 0.7 | 0.1 |
| Kidneys | 13.0 | 14.4 | 21.8 | 13.1 | 14.1 | 12.2 | 11.5 | 10.1 | 11.1 | 11.2 |
| B & U | 0.1 | 0.1 | 1.2 | 0.1 | 21.9 | 14.2 | 25.9 | 15.7 | 55.5 | 17.7 |
| Lung | 2.3 | 1.3 | 1.4 | 1.3 | 0.4 | 0.4 | 0.4 | 0.2 | 0.2 | 0.1 |
| Liver | 15.9 | 18.5 | 11.6 | 18.2 | 27.7 | 4.3 | 19.8 | 2.8 | 5.7 | 2.3 |
| Spleen | 0.6 | 0.3 | 0.3 | 0.3 | 0.1 | 0.1 | 0.1 | 0.0 | 0.1 | 0.1 |
| Stomach | 0.9 | 0.6 | 0.7 | 1.9 | 0.6 | 0.9 | 0.5 | 0.3 | 0.4 | 0.2 |
| SI&LI | 6.9 | 7.3 | 4.5 | 10.9 | 19.0 | 60.2 | 35.6 | 67.2 | 22.7 | 67.1 |
| Heart | 0.5 | 0.3 | 0.3 | 0.3 | 0.1 | 0.0 | 0.0 | 0.0 | 0.0 | 0.0 |
| Thyroid | 0.2 | 0.1 | 0.1 | 0.1 | 0.1 | 0.0 | 0.0 | 0.0 | 0.0 | 0.0 |
| Skin | 13.0 | 13.3 | 16.4 | 15.2 | 6.9 | 3.8 | 2.6 | 1.3 | 2.0 | 0.6 |
| Carcass | 2.8 | 10.4 | 4.2 | 7.8 | 1.4 | 1.0 | 0.5 | 1.2 | 0.2 | 0.2 |
| Inj.Site | 9.1 | 5.5 | 2.6 | 2.0 | 1.8 | 3.0 | 0.5 | 2.2 | 0.4 | 0.3 |

Example 20

Bile Duct Ligation Model of Liver Fibrosis

This bile duct ligation model was adapted from those previously described in the literature (e.g. Biecker et al. 2005 J. Pharm. Exp. Ther. 313(3)952-961; Martinez-Prieto et al. 2000 Clinical Science 98(5) 611-617; Ubeda et al. 1994 Hepatology 19(6) 1431-1436).

1. A male Sprague Dawley rat (180-200 g) abdomen was shaved and swabbed with betadine solution followed by 5 mg/kg carprofen s.c and 5 mg/kg buproprophine subcutaneously (s.c.).
2. Under Isoflurane anaesthesia a mid-line laparotomy was performed and the common bile duct located.
3. Bile duct was double ligated. The first ligation was made between the junction of the hepatic ducts and the second above the entrance of the pancreatic ducts.
4. Before closing ~2-3 ml saline was administered into the peritoneum.
5. Fascia and skin were closed and animals administered with 2 mg/kg metaclopromide s.c, 5 mg/kg Baytril s.c., and ~2 ml saline s.c.
6. Carprofen was given (5 mg/kg) as required over the next couple of days.
7. Control animals underwent sham surgery where bile duct was manipulated and a suture passed under the bile duct
8. Animals were closely monitored for the required period
9. On the biodistribution day under isoflurane anaesthesia animals were injected with 0.3 ml radiolabelled compound intravenously (i.v.) via tail vein (~2 MBq)
10. Organs were dissected at 5, 60 & 120 min post-injection (BDL animals).
11. Organs were dissected at 5, 60 & 120 min (Sham animals)
12. Radioactivity per gram of tissue in each organ was determined using a Wallac counter.

What is claimed is:

1. An imaging agent comprising a collagen binding peptide (CBP) and an imaging moiety, wherein said CBP is selected from:
   a) ANAALKAGELYKCILY-NH$_2$, SEQ ID NO. 18;
   b) ANAALKAGELYK-[Abu]-ILY-NH$_2$, SEQ ID NO. 19;
   c) Ac-ANAALKAGELFK-[Abu]-ILY-NH$_2$, SEQ ID NO. 35;
   d) Ac-ANAALKAGELYK-[Abu]-ILF-NH$_2$, SEQ ID NO. 20;
   e) Ac-ANAALKAGELY-[NMeLys]-[Abu]-ILF-NH$_2$, SEQ ID NO. 21;
   f) Ac-AN-[NMeAla]-ALKAGELYK-[Abu]-ILF-NH$_2$, SEQ ID NO. 22;
   g) Ac-AN-[NMeAla]-ALKAGELY-[NMeLys]-[Abu]-ILF-NH$_2$, SEQ ID NO. 23;
   h) ANAALKAGELYK-[Abu]-ILY-[PEG(4)]-[diglycolyl]-NH$_2$, SEQ ID NO. 19;
   i) ANAALKAGELY-[NMeLys]-[Abu]-ILY-[PEG(4)]-[diglycolyl]-NH$_2$, SEQ ID NO. 24;
   j) ANAALKAGELYK-[Abu]-ILY-[PEG(4)]-[diglycolyl]-COOH, SEQ ID NO. 19;
   k) D-YLI-[Abu]-KYLEGAKLAANA-NH$_2$, SEQ ID NO. 25; and
   l) GELYKCILY-NH$_2$, SEQ ID NO. 5;
   wherein "Ac" is an acetyl group, "Abu" is 2-aminobutyric acid, "NMeLys" is N-methylated lysine, "NMeAla" is N-methylated alanine, and "PEG(X)" is a polyethylene glycol chain of X units;
   and wherein said imaging moiety is either an integral part of the CBP or is conjugated to the CBP via a suitable chemical group.

2. The imaging agent of claim 1 wherein said imaging moiety is selected from:
   (i) radioactive metal ion;
   (ii) a paramagnetic metal ion;
   (iii) a gamma-emitting radioactive halogen;
   (iv) a positron-emitting radioactive non-metal;
   (v) a hyperpolarised NMR-active nucleus; and
   (vi) a reporter suitable for in vivo optical imaging.

3. A precursor for the preparation of the imaging agent as defined in claim 1 comprising the CBP as defined in claim 5 and a chemical group capable of reacting with a source of an imaging moiety, wherein said chemical group comprises:

(i) a chelator capable of complexing a metallic imaging moiety;

(ii) an organometallic derivative selected from a trialkylstannane or a trialkylsilane;

(iii) an alkyl halide, alkyl tosylate or alkyl mesylate for nucleophilic substitution; or, (iv) a functional group which alkylates thiol-containing compounds to give a thioether-containing product, and wherein said chemical group is either an integral part of said CBP or is conjugated to said CBP.

4. A pharmaceutical composition comprising the imaging agent as defined in claim 1 together with a biocompatible carrier, in a form suitable for human administration.

5. A kit for the preparation of a pharmaceutical composition, said kit comprising (i) the precursor for the preparation of the imaging agent of claim 3 and (ii) a biocompatible carrier, in a form suitable for human administration.

6. A method for the in vivo imaging in a subject of a condition in which collagen is formed, comprising administration of the pharmaceutical composition as defined in claim 4.

7. A method of monitoring the effect of treatment of a human or animal body with a drug to combat a condition in which collagen is formed, said method comprising administering to said body the imaging agent as defined in claim 1 and detecting the uptake of said imaging agent.

* * * * *